(12) United States Patent
Feichtinger et al.

(10) Patent No.: US 7,995,195 B2
(45) Date of Patent: Aug. 9, 2011

(54) METHOD OF OPTICALLY MONITORING THE PROGRESSION OF A PHYSICAL AND/OR CHEMICAL PROCESS TAKING PLACE ON A SURFACE OF A BODY

(75) Inventors: Heinrich Feichtinger, Hinteregg (CH);
Gottfried Rohner, Altstätten (CH);
Rudolf Jussel, Feldkirch-Tosters (AT)

(73) Assignee: Ivoclar Vivadent AG, Schaan (LI)

( * ) Notice: Subject to any disclaimer, the term of this patent is extended or adjusted under 35 U.S.C. 154(b) by 421 days.

(21) Appl. No.: 12/220,896

(22) Filed: Jul. 29, 2008

(65) Prior Publication Data

US 2009/0180118 A1    Jul. 16, 2009

(30) Foreign Application Priority Data

Jul. 30, 2007    (DE) .................. 10 2007 035 609

(51) Int. Cl.
*G01J 5/48*    (2006.01)
(52) U.S. Cl. ....................................................... 356/43
(58) Field of Classification Search .............. 356/43–50; 374/31–33
See application file for complete search history.

(56) References Cited

U.S. PATENT DOCUMENTS

| 4,890,933 | A | | 1/1990 | Amith | |
|---|---|---|---|---|---|
| 4,979,133 | A | * | 12/1990 | Arima et al. ................... | 702/134 |
| 5,123,739 | A | * | 6/1992 | Takenouchi et al. .......... | 356/319 |
| 5,501,637 | A | * | 3/1996 | Duncan et al. ................ | 374/126 |
| 5,762,419 | A | | 6/1998 | Yam | |
| 5,823,681 | A | * | 10/1998 | Cabib et al. ................... | 374/126 |
| 6,168,311 | B1 | * | 1/2001 | Xiao et al. ..................... | 374/161 |
| 6,796,144 | B2 | * | 9/2004 | Shepard et al. ............. | 65/29.11 |
| 2004/0182538 | A1 | * | 9/2004 | Lambrecht .................... | 164/457 |
| 2005/0244975 | A1 | * | 11/2005 | Rakow et al. ................... | 436/85 |

FOREIGN PATENT DOCUMENTS

| DE | 636199 | 10/1936 |
|---|---|---|
| DE | 26 44 299 | 1/1978 |
| DE | 257362 A3 | 6/1988 |
| DE | 689 16 447 T2 | 10/1994 |
| DE | 198 55 683 A1 | 6/1999 |
| DE | 101 44 695 A1 | 3/2003 |
| DE | 697 30 639 T2 | 9/2005 |
| DE | 10 2004 052039 A1 | 5/2006 |
| DE | 10 2006 009460 A1 | 9/2007 |
| EP | 0 714 023 A2 | 5/1996 |

* cited by examiner

*Primary Examiner* — Tarifur R Chowdhury
*Assistant Examiner* — Michael LaPage
(74) *Attorney, Agent, or Firm* — Ann M. Knab

(57) ABSTRACT

The invention relates to a method for optically monitoring the progression of a physical and/or chemical process taking place on a surface of a body in which the surface radiation which emanates from part of the surface during the physical and/or chemical process, is measured with the aid of a measuring device, in particular a sensor. In order to develop a method of this kind such that sintering processes can also be monitored in a firing furnace having thermal radiation equilibrium, the invention proposes to emit the radiation (14) having a radiation spectrum that differs from the surface radiation, to the surface (10) by means of a radiation source (15) and to measure the radiation with the aid of a measuring device (16).

23 Claims, 21 Drawing Sheets

METHOD OF OPTICALLY MONITORING THE PROGRESSION OF A PHYSICAL AND/OR CHEMICAL PROCESS TAKING PLACE ON A SURFACE OF A BODY

CROSS REFERENCE TO RELATED APPLICATIONS

This application claims priority to German Patent Application No. 10 2007 035 609.0 filed Jul. 20, 2007, which is hereby incorporated by reference.

The invention relates to a method for optically monitoring the progression of a physical and/or chemical process taking place on a surface of a body as claimed in the preamble of claim 1, in which surface radiation emanating from part of the surface is measured with the aid of a measuring device, in particular a sensor, and to an apparatus as claimed in claim 22.

Methods of the type mentioned initially are known and familiar to a person skilled in the art.

The course of thermally activated processes is generally controlled by continuously monitoring the temperature and correspondingly adapting the furnace power. Sintering in a firing furnace, in particular in a dental firing furnace, in which a ceramic mass is intended to be fired as perfectly as possible, may be mentioned as a typical example of such a process. This is usually effected by using a time/temperature curve, which is ascertained during numerous experiments, since an optimum firing result can be achieved with different combinations of the parameters of time and temperature within particular limits. Particular importance is attached to the measurement of the temperature in this case and, in absence of direct monitoring of the sintering progress, an optimum result can be achieved only by following an exact time/temperature curve.

Sintering success is usually monitored only after the firing process has been concluded, that is to say at a point in time at which corrections are no longer possible and the workpieces produced in this manner have possibly been rejected.

For this reason, an attempt has been made again and again to directly measure the progress of the sintering process. So-called Seger cones, which exhibit the combined influence of temperature and time in a defined manner by changing their geometry, are one known measure of this type. Apart from the complexity of such a method, interpretation of the change in the test specimen requires a large amount of experience when assessing the state of the actual firing batch.

Recently, different methods of "optical dilatometry" have been introduced, in which the change in length of an idealized test specimen is continuously monitored during the firing process with the aid of an image detection system. This method, however, is usually used only in ceramic research laboratories carrying out ceramic research, and it would potentially also be suitable for industrial applications, with the disadvantage, however, that also in this case the test specimen is an idealized test specimen, whose results cannot be directly applied to the industrial firing batch.

DE 41 32 203 describes an optical method for monitoring a melting or casting process. This process, however, is only suitable for measuring transformations that are accompanied by a strong heat transformation, such as in the case of a melting and solidifying process. In principle the process is based on the optical detection of the temperature holding or transformation point, which occurs when exceeding the phase transformation, wherein in contrast to usual optical temperature measuring processes the process does not require exact calibration since the temperature holding point can be determined from the discontinuity in the profile of the radiation intensity without requiring the exact knowledge of the temperature. Although the term "radiation intensity" is used in this connection, this method clearly belongs to the large group of optical temperature measuring methods and is by no means suitable for determining surface changes in a broader sense, and in particular in absence of any heat transformation.

In a similar manner EP-A2-191 300 describes the detection of the melting process of a metal alloy in a vacuum melting furnace. The change in the emissivity of the surface that simultaneously occurs at the temperature holding point, by tearing open the oxide film on the molten material, however, is regarded as a disruptive effect in this patent, which makes the perfect detection of the melting point by analysing the progression of the radiation intensity more difficult, and measures are proposed with the help of which the disruptive effect on the optical temperature measurement can be excluded. This disruptive effect in particular, however, i.e. the changes in the radiation intensity in chemical and/or physical processes that are not influenced by the temperature, is the object and core idea of the present invention, which does not look into the problems of optical temperature measurement.

Similarly, most of the instructions for use for optical pyrometers include warning comments in case the temperature is to be exactly measured for example during the progress of a physical or chemical transformation or during a sintering process. Since the emissivity can change during the course of processes of this kind, it is recommended to continuously change the corresponding setting at the optical pyrometer as otherwise the measured temperature values are not true. It is this measuring difference in particular, which occurs at optical pyrometers which have not been reset, i.e. which have been set to a constant emissivity, and it is a difference that does not result from the change in temperature itself but from the change in the optical properties and/or the topography of the measured surface, which according to the concept of the invention is used for determining a physical and/or chemical process. Contrary to all optical methods mentioned before, which are only capable of detecting reactions of the kind in which a heat transformation occurs, the method according to the invention thus is also capable of detecting processes in a metrological manner, in which no heat exchange with the environment takes place.

Before describing the method of the invention in more detail, some of the terms essential for the method are to be described closer. The emissivity describes the radiation behavior of a surface in comparison to a black body. A black body of this kind comprises a hypothetically idealized surface, which completely absorbs any electromagnetic radiation striking it irrespective of the frequency. According to Kirchhoff's law of radiation, absorptivity and emissivity of a body are always proportional to each other, and since the black body has an absorptivity as large as possible of 100% for any wavelength, it emits the maximum thermal radiation power at any temperature. This radiation is direction-independent and therefore is of diffuse character and is described by means of Planck's radiation law.

In contrast thereto, the surface of a gray body absorbs only part of the impinging radiation, which results in the fact that also less radiation is emitted than in the case of the black body. The ratio of the radiation quantities is expressed by the emissivity e which can assume values between 0 and 1. The value 0 applies for a hypothetically white body, which does not absorb any radiation but completely reflects the radiation, the value 1 applies for the black body, which absorbs the entire radiation and does not exhibit any reflectivity. In reality, most of the bodies belong to the group of gray emitters and therefore possess some degree of absorptivity and simultaneously reflectivity. In the case of transparent materials such as glasses there is also the transmissivity, wherein the sum of these three properties always is 100%. As a result of the reflectivity, the radiation behavior of gray bodies is direction-dependent when compared to black bodies. The amount of radiation from a surface received from a detector, thus, on the one hand, depends on the emissivity and through the influence of the directional dependancy, on the other hand, also on the topography of this surface.

The conditions of the black body can be fulfilled in practical approximately with the aid of the concept of a cavity emitter. This is a space of constant temperature closed by all sides, into which no extraneous radiation enters, i.e. there is an equilibrium between absorbed and emitted radiation. Such conditions, for example, roughly occur in sintering furnaces well thermally isolated, in which the temperature is only changed slowly, i.e. furnace content, heating elements and furnace walls have approximately the same temperature and the emissivity under such conditions is practically 1. This is an ideal precondition for a precise optical temperature measurement, since changes of the optical properties and/or of the topography of a surface located in a space of this kind do not affect its radiation behavior anymore.

On the basis of the disadvantages explained and acknowledging the prior art revealed in the case of methods of the type mentioned initially, the present invention is therefore based on the object of developing a method as claimed in the preamble of claim 1 and an apparatus as claimed in the preamble of claim 17 in such a manner that also processes of the kind can be monitored that do not exhibit a heat transformation, with the aid of which, for example, a melting or solidifying process is detected using the holding point that occurs. Moreover, it is also intended to be able to detect processes under the conditions of cavity radiation, for example a sintering process, in which the batch is in a temperature equilibrium with the furnace.

According to the invention, this object is achieved by means of claim 1. Advantageous developments emerge form the subclaims.

According to the invention, extraneous radiation (14) is radiated on the surface (10), wherein changes in the emissivity and/or topography occurring as a result of chemical and/or physical processes lead to a changed portion of the reflected extraneous radiation and therefore of the intensity of the radiation (13) reaching the detector (16).

In a first alternative of the concept of the present invention, the extraneous radiation (14) can originate from surfaces in the surrounding area of the body (11) that radiate on its surface, said surfaces varying due to the deviant temperature of the spectrum radiated from the surface as result of the characteristic temperature of the spectrum such that the radiation intensity of the radiation (13) detected by the detector (16) also contains reflected portions of the extraneous radiation (14). The quantity of the portion of reflected extraneous radiation depends on the emissivity and/or the topography of the surface (10), and if a change of one of these criteria occurs as a result of a physical and/or chemical reaction, a discontinuity in the temporal profile of the curve of radiation intensity detected by the detector occurs. This method variant therefore presupposes a natural radiation disequilibrium between the surface (10) and at least parts of its environment.

A firing process of a dental restoration part may be mentioned as an example for this method variant, which takes place in small furnaces and in a few minutes only. In order to implement the high heating speeds, the heating coils have a temperature which is considerably higher than that of the dental firing batch. The extraneous radiation (14) emitted by the heating coils and radiated on the firing batch therefore has a higher and more intensive portion of short-wave radiation; a part of this radiation is reflected and reaches the detector (16) as part of the radiation (13). However, with this mode of operation, a reaction can only be detected if the temperatures in the furnace are constant or change in a constant manner, since any immediate change of the time/temperature curve generates a discontinuity of the radiation intensity at the detector (16) as well, and a simultaneous reaction taking place on the surface (10) can therefore be overlooked. The sensitivity of the detection of reactions of course decreases with the degree, to which a radiation equilibrium between the surface (10) and the environment develops. When compared to a dental firing furnace this applies to the later stage of the firing process, in which the firing batch has largely approximated to the temperature of the heating coil and the furnace walls.

For the conduction of this first method alternative, for example a quotient pyrometer can advantageously be used. Pyrometers of this kind measure the radiation intensity simultaneously at two different wavelengths, the ratio of the intensity then being characteristic for a specific temperature, since the intensity of each wavelength changes according to Planck's spectrum in a characteristic manner. Provided that the intensity of both wavelengths is influenced by the emissivity in an identical manner, which approximately is the case with "gray bodies", the emissivity then is irrelevant for the measurement of the temperature. Thus, any pyrometer having two channels, apart from its object to measure the temperature, in the inventive sense can also be used to detect reactions with one of its channels, however, under the precondition that the temperature of the monitored surface (10) is constant or changes in a constant manner and that this surface is not in radiation equilibrium with the environment. With a pyrometer modified in such a manner, the temperature dependancy of a reaction can be elegantly represented in a time- or temperature-dependent diagram, the quotient measured value of both channels providing the temperature value and the measured value of one of both channels providing the reaction characteristic value. With reference to the example of a sintering process taking place in a furnace which has been heated with constant speed, the heating power of this furnace can be reduced after the occurrence of a discontinuity of the intensity curve of the detector (16), wherein the further course of the sintering process, however, is superimposed by the discontinuity caused by the change of radiation from the heating elements due to a reduction of the furnace power, and cannot be exactly traced any longer.

A second preferred variant of the method of the invention uses extraneous radiation (141) of a radiation source (15) which is projected onto the surface (10) of the body (11), the reflected portion thereof in an analogous manner as described above then reaches the detector (16) as part of the radiation. The wavelength of this extraneous radiation (141) advantageously is selected to be in a range, which occurs in the natural self-radiation of the surface (10) to a very small extent or does not occur at all. The sensitivity maximum of the detector (16) is also selected to be in the wavelength range of the extraneous radiation (141), such that only the change in intensity of the portion of the extraneous radiation (141) reflected from the surface (10) is detected by the detector (16). This means, that for thermally activated processes the wavelength of the radiation source (15) should preferably be selected to be in a considerably higher temperature range than would correspond to the temperature of the surface (10) and its environment, that is to say for example in the range of blue light or even in the range of close UV light. If a broad-band detector were selected in such a case, which also detects portions in the red or infrared range of the spectrum, the radiation (13) can be advantageously transmitted through a filter that eliminates the longer-wave radiation such that only those changes in radiation intensity are detected by the detector (16) that are based on reaction-triggered changes in the emissivity and/or the topography of the surface (10).

Both alternatives of the method thus are based on the same central core of the inventive concept, that is to say the use of a radiation disequilibrium, i.e. the measurement of the portion of the extraneous radiation reflected from the surface (10) within the radiation (13) emitted from this surface by means of the detector (16). This first alternative uses surfaces, which naturally exist within the environment of the surface, as sources for extraneous radiation, and the second alternative achieves the same object by using a deliberately selected radiation source (15). The advantage of the second alternative of the method is not only the fact that a temperature measurement and a detection of the progression of a chemical and/or physical reaction can be completely separated from the metrological view, but also in the case of cavity radiation, i.e. in a furnace, for example, in the inner chamber thereof completely homogeneous temperature conditions exist, to eliminate this radiation equilibrium by the extraneous radiation (141) of the radiation source (15) relative to the surface (10).

In a further advantageous refinement it is provided that the radiation (13) is measured by several sensors that are arranged in the form of a pixel matrix, wherein each of these sensors represents part of a radiation (13) emanating from a part of the surface (10) in the form of an intensity curve, and a discontinuity of this curve in the sense described so far as a result of changes in the emissivity and/or the topography of this part of the surface (10) provides information on the progression of a physical and/or chemical process caused by it, wherein by combining the different profiles of curves of adjacent pixels additional information is gained that predominantly gives information about changes in the topography of the area (10).

One advantageous refinement of the invention provides that a test specimen with a defined geometry is used. A test specimen of this kind, for example, can be a pointed cone having a point that increasingly becomes round under the influence of liquefaction and surface tension. Seger cones can also be used that in the technology of ceramic firing are known as standardized test specimen. According to the invention it can be observed how the particles of powder specimen or green bodies in a first phase form sintering necks at contact positions with neighboring particles in a first stage under the influence of the surface diffusion. Conventional methods for controlling the sintering process, such as dilatometry, can hardy detect this first phase since it is accompanied by a change in volume and length of the test specimen that cannot hardly be measured. The method according to the invention, however, already shows a clear change in the optical properties of the surface in this phase. In a second phase, which is accompanied by clear changes in volume, due to the process of volume diffusion, an increasing coagulation of the particles is taking place, wherein at the same time the volume of the cavity is decreasing. An optical dilatometer can also trace the process in this phase based on changes in length accompanying it, wherein, however, it requires an idealized test specimen of defined dimension and shape for this purpose, whereas the method according to the invention can be employed at any surface of the actual firing batch.

The increasing mobility of the atoms and molecules in the micro-region leads to a smoothening of the rough topography of the surface, which initially is defined by the original particles, the smoothing taking place under the influence of the surface tension in its attempts to minimalize the surface, thus increasing its reflectivity. The surface tension, however, at longer periods of time is also effective in the macroscopic region, i.e. a test specimen with a given acute-angled geometry will truncate or blunt its peak, which is increasingly becoming smoother and thus more reflective, into a spheroidal shape in the course of time. Thus, besides the primary influence of the change in reflectivity of the individual surface elements, at the same time the radiation angles of this radiation change due the macroscopic change in topography, which based on the relative change in the intensity curves of neighboring pixels of a detector matrix can be used to characterize the course of firing, in analogous manner for example to the descent of Seger cones or to the usual determination of the hemisphere temperature point in the ceramic technology.

In a further advantageous refinement of the invention it is intended to use any other bodies that have been formed in a defined manner according to the invention. For example, it is possible to use bodies with several peaks having different pitches or opening angles, and it is also possible to assess the influence of surface tension in a half-quantitative manner.

In the sense of this method alternative, for example, a video camera in the visible range or in the range of the close UV light can be regarded as a pixel matrix, wherein the video camera is equipped with a lens suitable for the purpose of observing the surface (10), as well as with an image analysis software, which allows to evaluate the radiation intensity that occurs at each pixel and optionally also the color value of the radiation after digital conversion with regard to the intensity profile in one or also simultaneously in several wavelength ranges.

As in the case of a single detector, the information achieved in this way can be used as a control variable for changing the parameters of a facility, in which the physical and/or chemical process is taking place, in order to thereby exert an influence on its progression. In the case of a furnace this would be the heating power, for example. If a plurality of detectors is used in the sense of a pixel matrix, however, then the information can be represented illustratively on a display by marking certain regions of the surface (10) in which the process has reached a certain stage, with color errors or hatching, such that the observer immediately gains an impression on the progression of the reaction in the area observed. In the case of a UV camera, the signals of the detectors of the pixel matrix must be transposed in total to the visible range in order to be represented on a display, wherein certain stages of the reaction can also additionally be identified with the aid of color errors or hatching.

Another advantageous refinement provides for the physical and/or chemical process to be carried out as part of a phase transformation.

Another advantageous refinement provides for the physical and/or chemical process to be carried out as part of heat treatments and/or thermochemical processes.

Another advantageous refinement provides for the temperature of areas of the surface to be measured, the measurement being carried out using a voltage-forming or current-forming method, in particular a thermocouple or temperature-dependent resistor.

Another advantageous refinement provides for the temperature of areas of the surface to be measured using an optical method, in particular a quotient pyrometer, the intensity profile of at least one of the wavelengths of the quotient pyrometer for measuring the radiation intensity of the process and the combination of intensities of the measured values of both wavelengths of the quotient pyrometer being used in a conventional manner to determine the temperature.

Another advantageous refinement provides for the process to be carried out as part of a sintering process which is a firing process that takes place in a dental firing furnace.

Another advantageous refinement provides for a measuring device, in particular a sensor, to be at a distance from an area of the surface.

In addition to the measuring device, in particular at a distance from the latter, another advantageous refinement provides for a radiation source to be at a distance from an area of the surface, and, in particular, for the optical axis of said radiation source to be aligned with respect to the surface.

Another advantageous refinement provides for the measuring device to be an optical sensor or a matrix of sensors.

Another advantageous refinement provides for the measuring device to have focusing optics.

Another advantageous refinement provides for the radiation source to be a light source, for example a lamp with a broader or less broad wavelength range, preferably a LED, a halogen lamp or a laser.

Another advantageous refinement provides for a measuring device and a radiation source to have optical axes which are arranged in such manner that the reflection of the radiation is detected, at most, by the measuring device.

Another advantageous refinement uses polarized radiation by polarizing the light of the radiation source by means of a polarizing filter before it strikes the surface of the test specimen, and wherein the light reflected by the surface of the specimen reaches the detector by passing a rotatable polarizing filter that is embodied as an analyzer, wherein the polarized light can be used in a known manner as an identification of optically active substances.

Another advantageous refinement provides for the measuring device and the radiation source to be arranged on a common holding apparatus, both the measuring device and the radiation source being able to be moved at least in one direction, preferably on the plane determined by their two optical axes.

Another advantageous refinement provides for a semipermeable mirror which can be used to insert the radiation into the optical axis of the measuring device to be situated in the beam path of the measuring device.

Another advantageous refinement provides for the measuring device and/or the radiation source to be components of a furnace, the radiation and the surface radiation being measured through an opening in the furnace that is preferably provided with a window which transmits the radiation and surface radiation.

Another advantageous refinement provides for the holder to be able to be moved in at least on spatial direction.

Further advantages, details and features of the invention emerge from the following description of the exemplary embodiments of the invention using the drawings, in which.

Figure 1:
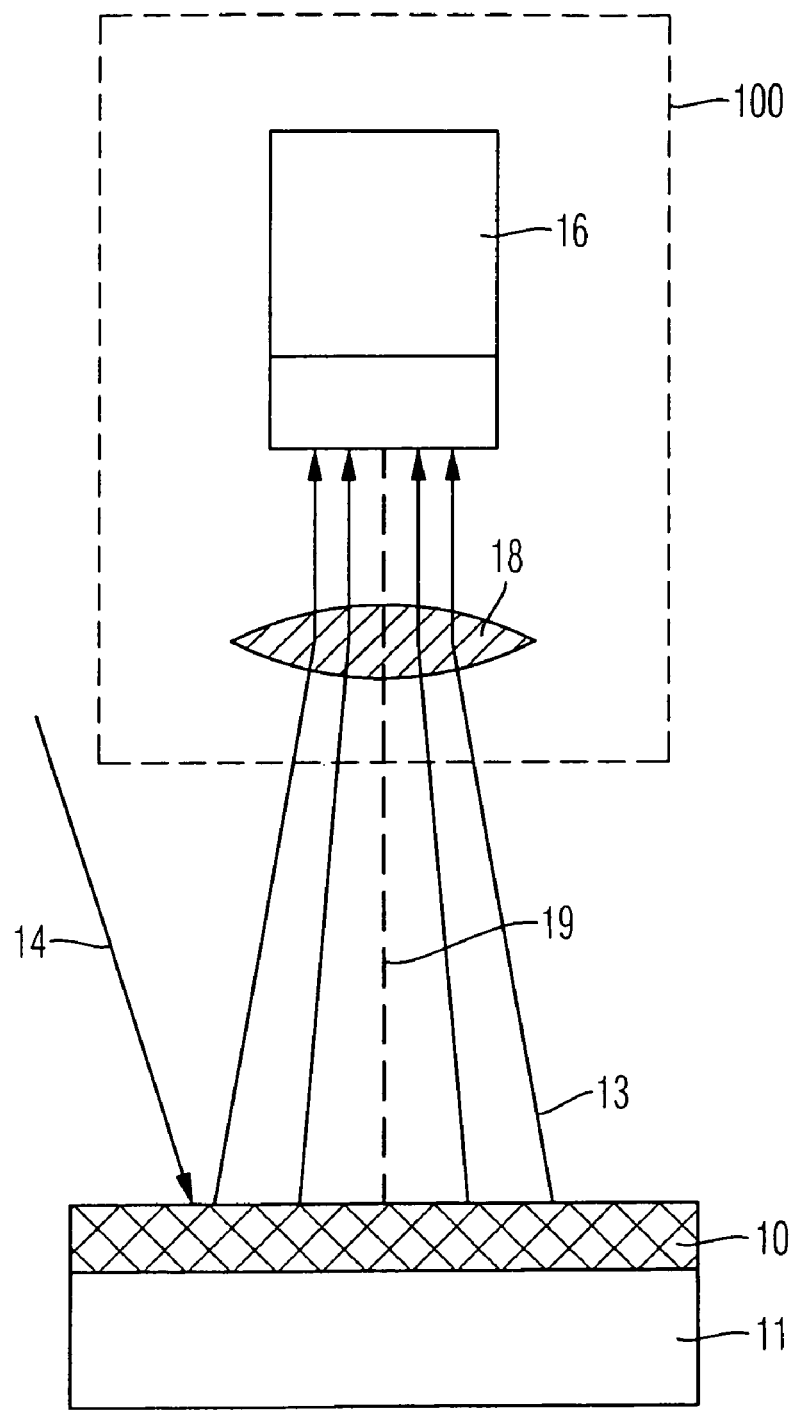
FIG. 1 shows a diagrammatic illustration of the first embodiment of the method according to the invention, which embodiment is specially suitable for furnaces in which there is no thermal equilibrium between the furnace walls and the batch.

FIG. 1 shows a method for optically monitoring the progression of a physical and/or chemical process taking place on the surface 10 of a body 11, in which part of the extraneous radiation 14 radiating on the surface 10 is reflected and together with the temperature-corresponding natural radiation of the surface 10 reaches the measuring device 16 in the form of a sensor as radiation 13 via a focusing lens system along the optical axis 19.

In the most general case, the extraneous radiation 14 can come from one or more bodies in the surrounding area of the surface 10, however, it is important that this extraneous radiation has a characteristic that differs from the temperature-corresponding natural spectrum of the surface 10 in order that the change of the portion of the extraneous radiation 14 reflected by the surface 10 can be detected as a change of the total radiation 13.

As an example, the surface 10 can belong to a body that is intended to be sintered in a furnace and the measuring device 16 can be an IR sensor, like a sensor that is employed for the purpose of measuring the temperature by measuring the radiation intensity in a wavelength range.

For this example it is assumed that the furnace is heated with steady velocity. In order to necessitate a sufficient heating velocity, the heating element of the furnace thus always needs to have a temperature that is higher to a certain extent, such that the extraneous radiation 14 emitted by the heating element has a radiation spectrum that is shifted towards shorter wavelengths. A conventional ceramic or metallic green body forms an accumulation of loosely bound particles with a plurality of microsurfaces that are inclined towards different spatial directions. This results in a low emissivity, that is to say the incident extraneous radiation is diffusely spread, as it is generally the case for unfired ceramics whose emissivity is in the order of 0.6 to 0.8. Although the angle of incidence of the hotter extraneous radiation in FIG. 1 leads to an angle of reflection that would bypass the detector, a larger portion of the diffusely reflected radiation nevertheless reaches the measuring device 16 due to the strong scattering effect of the non-sintered surface 10, resulting in the fact that the radiation intensity detected by the measuring device being higher than it would correspond to the natural temperature of the surface 10. This is a situation in which the conventional methods for optically measuring the temperature fail, however, this effect is essential and advantageous for the method according to the invention.

During the first part of the heating process the radiation intensity detected by the measuring device 16 increases due to the steady increase in temperature of the heating coil and also of the surface 10. As soon as sintering necks are formed, that is to say as soon as neighboring particles start to bond under the influence of surface diffusion and sharp edges are increasingly smoothed under the influence of surface tension, the scattering effect and the emissivity are reduced. Thus, an increasing part of the extraneous radiation is reflected past the measuring device 16, which manifests itself in a suddenly occurring reduction of the intensity 13 that can be detected in form of a discontinuity.

Figure 2A:
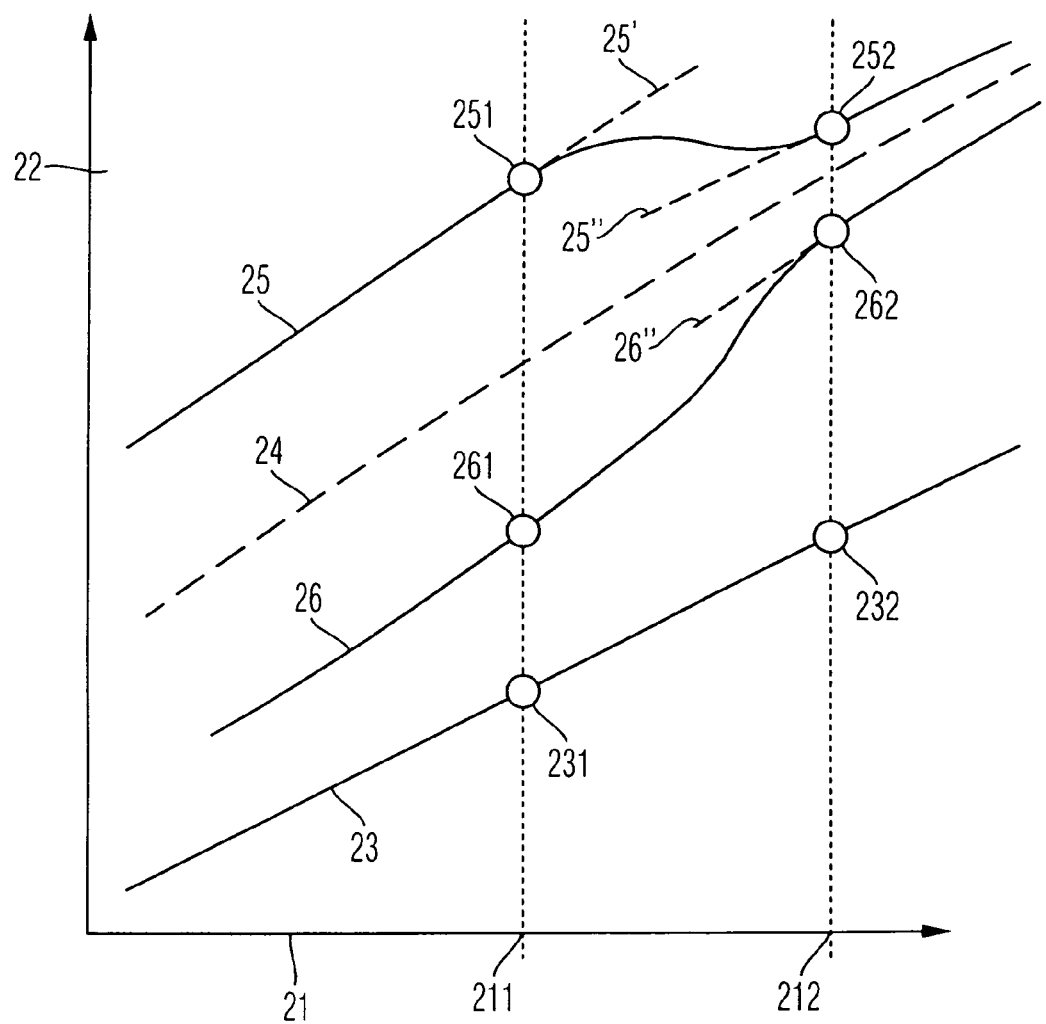
FIG. 2a shows a diagrammatic illustration of the temporal profile of the radiation intensity of a surface in the course of heating a furnace according to FIG. 1, during which a chemical and/or physical transformation takes place occurs at a particular point in time.

FIG. 2a shows a diagrammatic illustration of the temporal profile of the radiation intensity measured under such conditions. In this case, 21 denotes the time axis and 22 denotes the axis of intensity of the radiation of the surface 10 determined by a measuring device, whereas the surface, in this example being uniformly heated according to the temperature curve 23. The curve 24 shows the hypothetical profile of the intensity of a black body whose profile is influenced only by the temperature and whose profile is therefore similarly continuous like that of the temperature curve 23.

The curve 25 shows the progression of the radiation intensity of a gray body which—as described in FIG. 1—is located in predominantly a hotter surrounding area, in which case it is assumed that this body is an unsintered ceramic mass. Such a mass shows a high emissivity, e.g. in the range of 0.8, and is thus close to the behavior of the black body and therefore reflects only to a slight extent. However, with the considerably higher temperature of the surrounding area, this low reflectivity nevertheless results—caused by the spreading effect of the surface 10—in a considerable additional amount of radiation being reflected to the measuring device 16 via the surface 10, which is shown by the fact that the curve 25 runs in an approximately parallel manner above the curve 24 for the black body till the point 251.

At the point 251, there is an increasing deviation of the curve 25 from the curve 25', which was constructed in front of the point 251 on the basis of the regressed behavior of the curve; the curve 25', however, can also be considered to be a tangent, i.e. a first derivate of the function 25 at the point 251. In this sense, the point 251 can also be determined in a conventional manner by using the first and/or second derivate of the regressed curve function. The negative deviation of the curve after the point 251 at the point in time 211 shows that the emissivity is shifting to lower values, which is associated with the increasing reflectivity of the surface 10 which is increasingly being sintered.

The beginning of the sintering process can thus be determined at the point in time 211 and/or the temperature 231.

As the sintering process progresses with an increasing period of time and a rising temperature, the emissivity is reduced further, which results in a further reduction in the radiation intensity of the curve 25. At the point 252, the curve 25 enters a continuous profile again which is virtually influenced only by the temperature. The point 252 can be determined in a similar manner to the point 251 by back-extrapolating the section of the curve produced after the time 212 in the form of the curve 25" or applying the tangent of the function at the point 252. The point 252 thus shows the return to an almost constant emission behavior and the time 212 and the temperature 232, at which the firing process resulted in a homogeneous product, are thus found.

In the case of relatively long periods of time after the time 212 and above the temperature 232, the curve 25 increasingly approximates the hypothetical curve 26 of the black body. This has nothing to do with a change in the emissivity of the surface 10 but rather results from the fact that, in the case of relatively long periods of time and temperatures, the temperature of the specimen and the colder and hotter zones of the furnace wall are increasingly balanced, as a result of which the situation approximates that of cavity radiation which corresponds to the ideal behavior of the black body.

The curve 26 corresponds to the conditions in a furnace, in which the surface 10 is only surrounded by colder bodies. The extraneous radiation 14 thus contains radiation, which is shifted in its spectrum towards longer wavelengths and lower intensity and accordingly, the profile of the curve 26 is below the one of the curve 24, which describes the behavior of the black body which is not influenced by the surroundings. At the point 261 the sintering process begins, contrary to the previous example now it is assumed that an increasing proportion of the more energized or energy-richer radiation 13 reaches the detector, which results in a rise of the curve 26.

If the same sintering process were carried out in a slowly heated furnace, in which the temperature of the furnace and the batch, that is to say the furnace walls and the body 11, were almost identical during the heating process, an almost perfect radiation equilibrium would exist from the start, as a result of which the curves of the gray body 25 and 26 would always be closely above and below the curve 24 for the black body. In such a case a change in the emissivity of the surface 10, which change is triggered by a chemical and/or physical process, would be manifested only slightly or not at all in the curves 25 and 26.

Figure 2B:
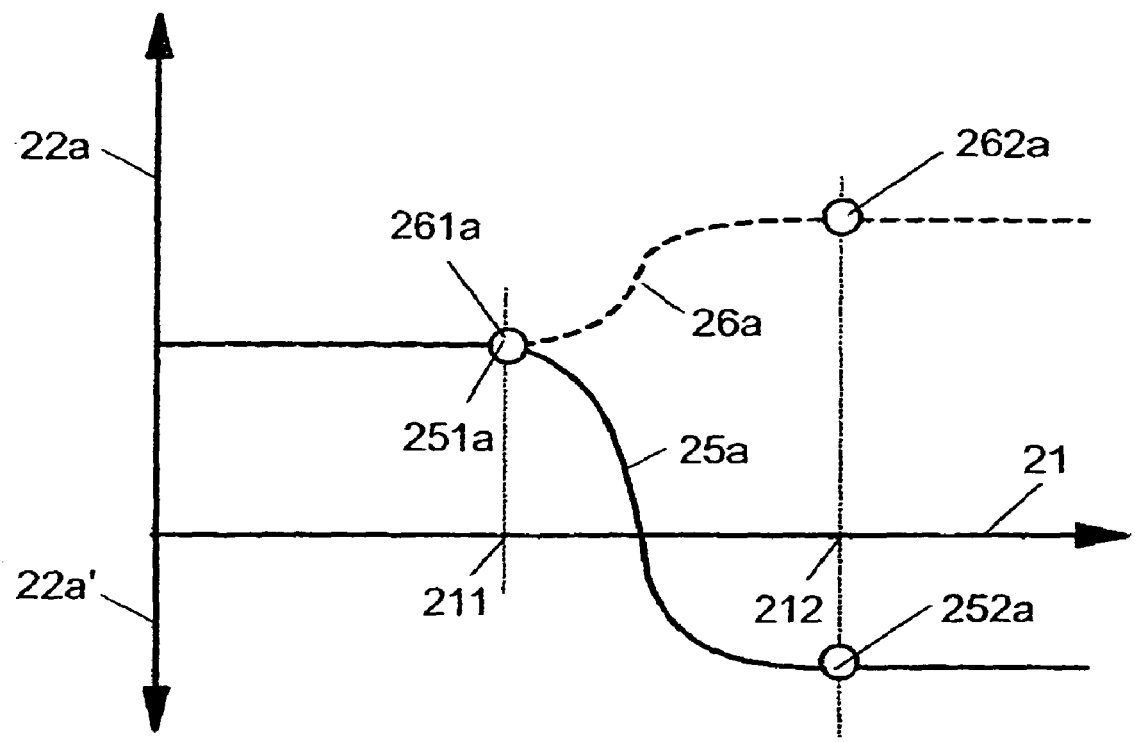
FIG. 2b shows a diagrammatic illustration of the profile of the first derivative of the radiation intensity curves that have been shown in FIG. 2.

FIG. 2b shows the first derivatives 25a and 26a of the curves 25 and 26 in FIG. 2a. The reaction-dependent discontinuities 251a and 261a at the beginning and 252a and 262a at the end of the sintering process are much better visible in this graphical representation since the influence of the changing temperature conditions no longer predominates.

Figure 2C:
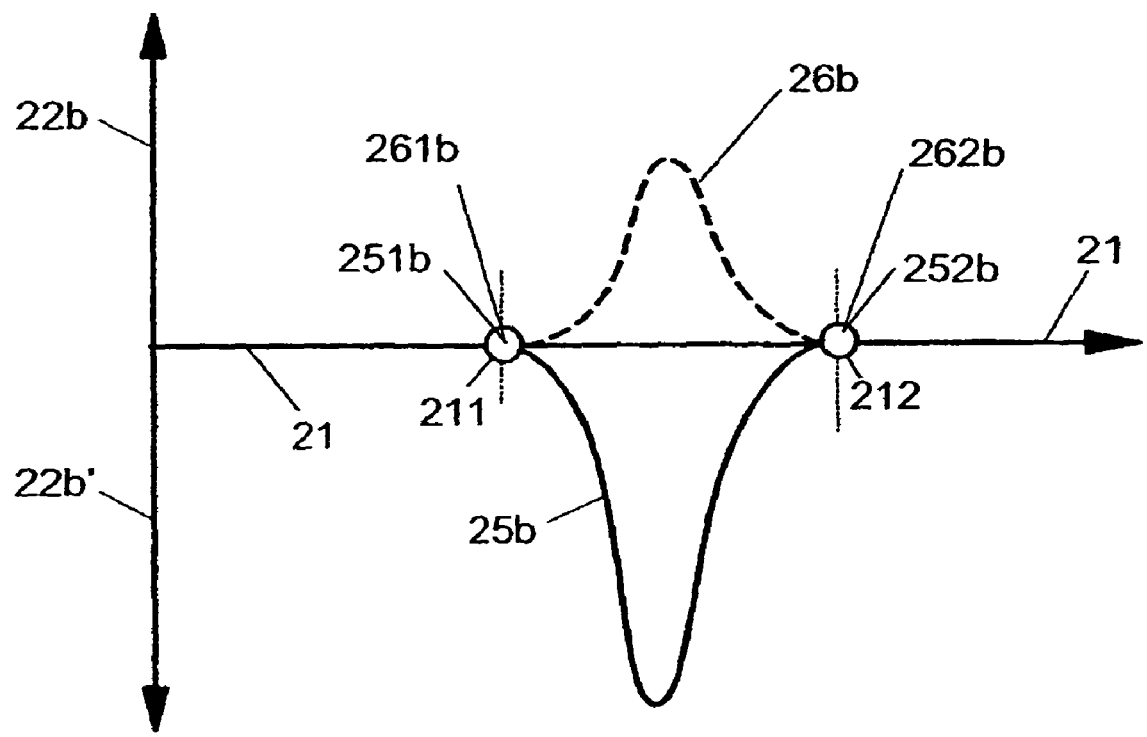
FIG. 2c shows a diagrammatic illustration of the profile of a second derivative of the radiation intensity curves that have been shown in FIG. 2.

FIG. 2c shows the second derivatives 25b and 26b of the curves 25 and 26 in FIG. 2a. Here, the influence of the temperature is completely suppressed and the reaction is marked in a descriptive manner by the peaks beginning at the point in time 211 with the point 251b and ending at the point in time 212 with the ending points 252b and 262b. The apex of these peaks corresponds to the maximum of the optical rate of change of the surface 10.

With the processes described so far and the curves resulting from it, it was exemplarily assumed so far that a sintering process is described which naturally results in a decrease of the emissivity due to the increasingly smoothing surface. However, it is also conceivable to use processes whose surface behavior is exactly the opposite way around, e.g. when nitrating a metal surface as part of a thermochemical coating. In this case, the initially shiny or glossy surface has a low emissivity, e.g. in the range of 0.05-0.15, which shifts to higher values after the formation of the first nitration layer.

Figure 3A:
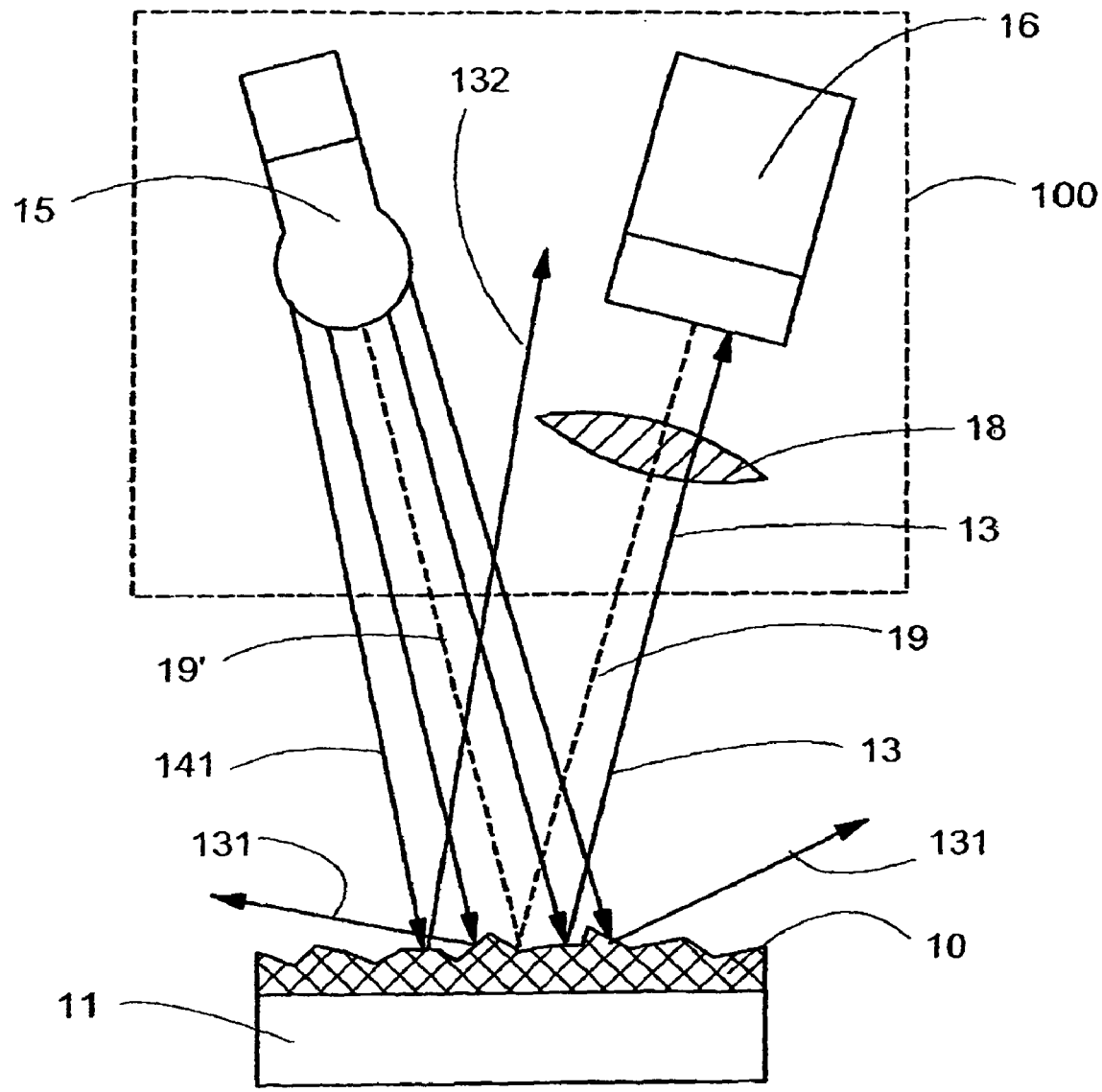
FIG. 3a shows a diagrammatic illustration of the second embodiment of the method according to the invention, comprising a radiation source (15) that radiates on a surface having a rough topography.

FIG. 3a shows the second alternative of the method according to the invention which allows the method to also be used in a furnace which is virtually in thermal equilibrium. In this case, a light source as radiation source 15, preferably a lamp, which is fastened outside the furnace wall or on the periphery of the furnace to the side of the measuring apparatus 16 projects extraneous radiation in the form of the beam 14 onto the surface 10 of the body 11 which has a complex topography in this stage. In this case, the wavelength or wavelength range of the radiation 14 is advantageously selected in such a manner that it corresponds to a range of low intensity inside the spectrum of the natural thermal radiation of the surface 10. In the sense of a specific example, a sintering process in the temperature range of from 700-1000° C. is intended to be monitored, for example. The wavelength range of the light source could advantageously be selected to be in the range of blue light, for example close to 400 nm which corresponds to a temperature in the range of above 5000 K, for such a measurement.

This produces conditions for the surface 10 which prevail in a furnace that is in thermal disequilibrium and the light source 15 effectively assumes the role of furnace walls at a considerably higher temperature. The intensity profile detected by the measuring device 16 is then similar to the profile of the curve 25 in FIG. 2.

In the embodiment shown in FIG. 3a, the radiation 14 from the radiation source 15 is projected onto the surface 10 at a particular setting angle and is supplied from there, together with the surface radiation 13 on the surface 10, to the measuring device 16 in the form of a sensor via focusing optics 18. The radiation source 15 and the measuring device 16 form the apparatus 100. The wavelength of the radiation source 15 is matched as exactly as possible to the highest sensitivity range of the measuring device 16. In addition, according to the method, a wavelength which occurs only with a low intensity in the radiation spectrum of the surface radiation 13 at the measurement temperature is selected. Even if the body 11 is in the state of cavity radiation, that is to say if there is radiation equilibrium, the change in the emission factor of the radiation 14 and/or of the surface radiation 13 can be determined on the basis of the radiation disequilibrium caused by the radiation 14 using the apparatus 100.

In this case, the topographic effect of the surface 10 becomes apparent which is not to be mistaken for the spreading effect associated with the emissivity. In accordance with the local inclination of the surface, a part of the radiation 141 is reflected off the measuring device at the point of incidence e.g. in the form of the beams 131 and 132, and only the beam 13, which is reflected approximately parallel to the optical axis 19 due to the locally horizontal inclination of the surface, reaches the detector.

Figure 3B:
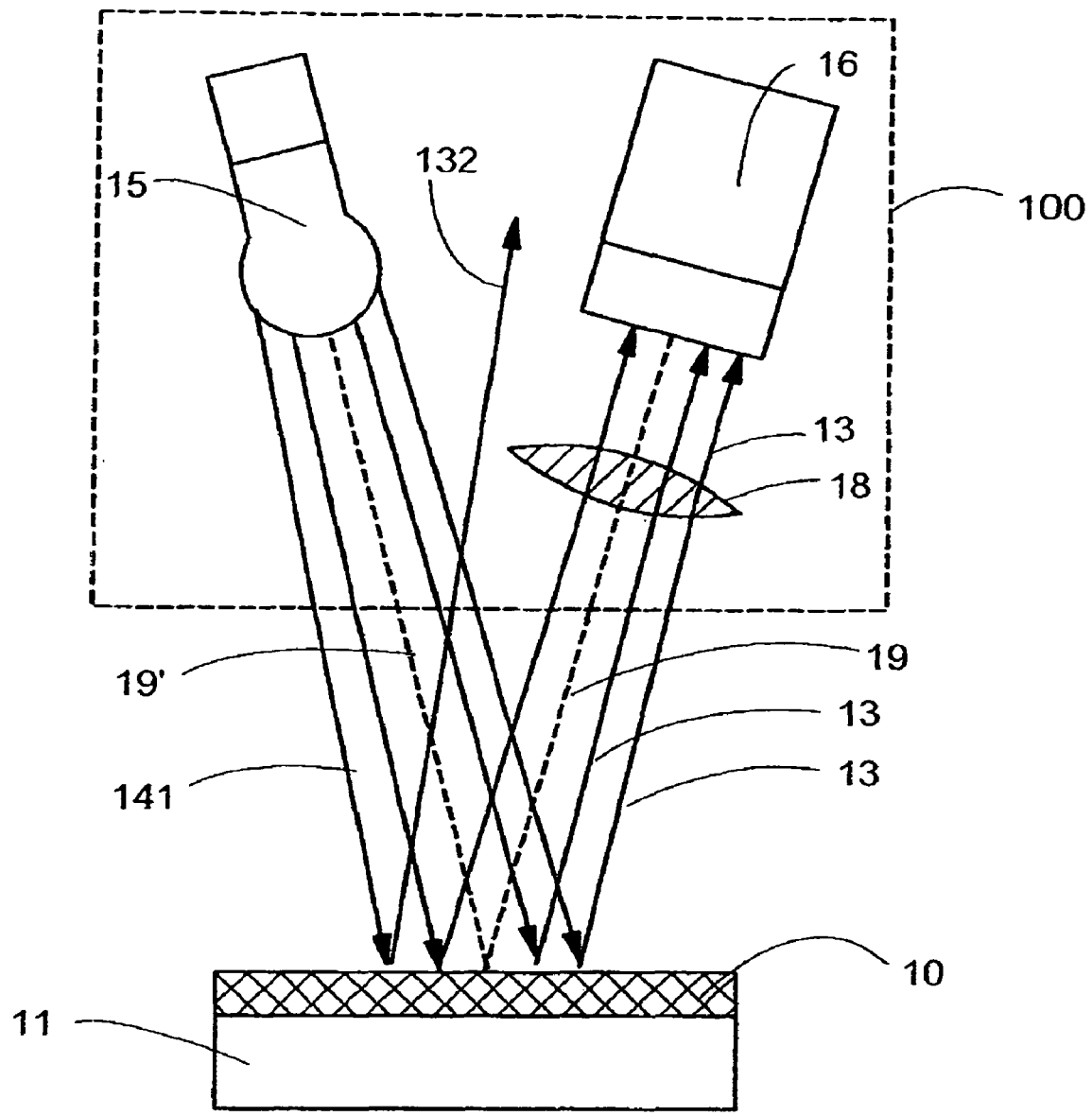
FIG. 3b shows a diagrammatic illustration of the second embodiment of the method according to the invention, comprising a radiation source (15) that radiates on a smooth surface.

FIG. 3b shows the same arrangement as FIG. 3a, whereas the surface 10, however, under the influence of a reaction has become smooth in the horizontal direction, as a result of which only a part of the radiation passes the measuring device according to arrow 132, the remainder of the radiation 13 reaches the detector and is detected as an increase in the radiation intensity thereof.

Figure 3C:
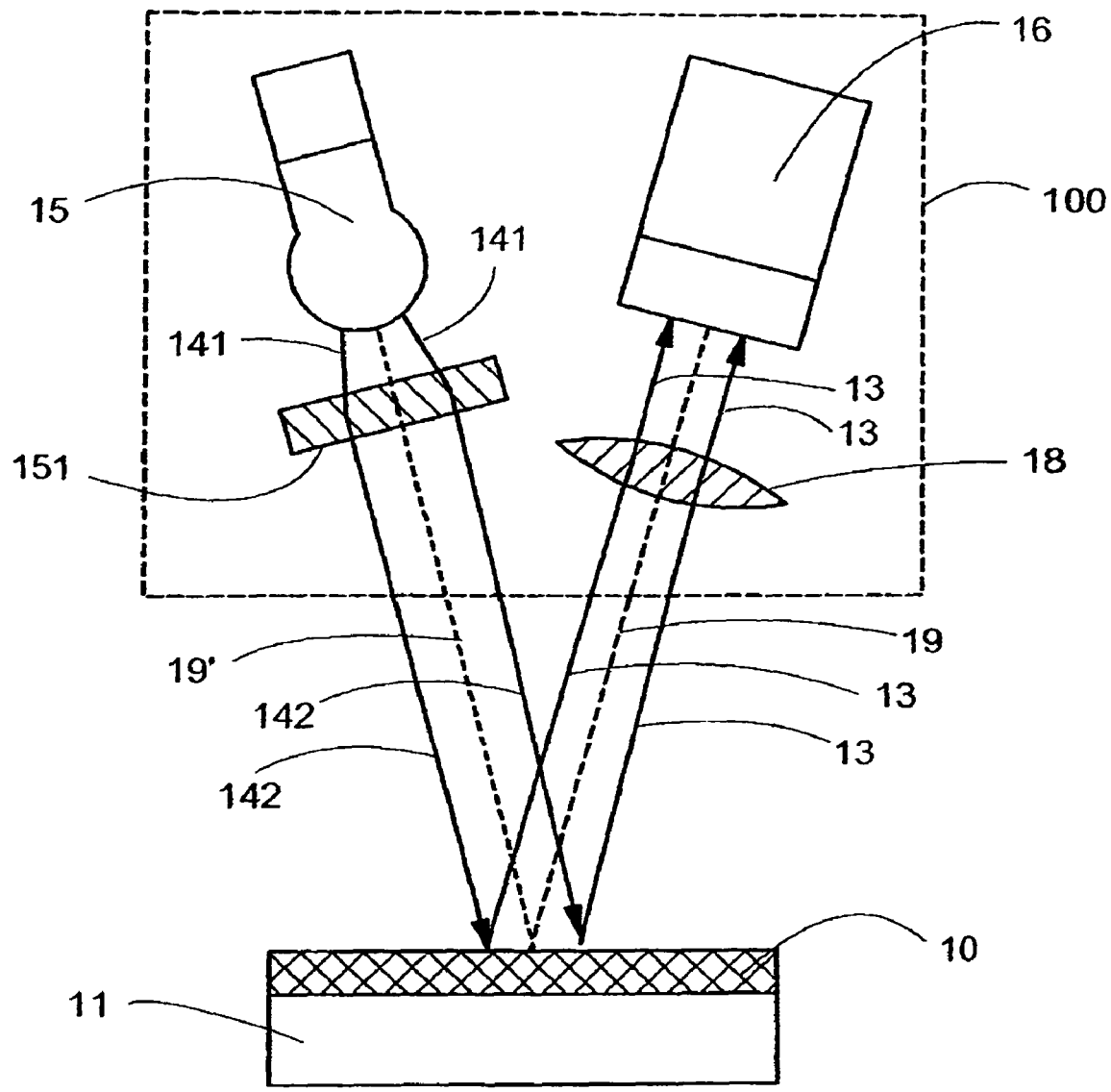
FIG. 3c shows a diagrammatic illustration of the second embodiment of the method according to the invention, comprising a radiation source (15) and a collimator (151)

FIG. 3c shows the same situation as is shown in FIG. 3b, whereas in this case, however, a collimator 151 was inserted in front of the radiation source 15 in order to bundle or concentrate the divergent radiation 141 into the directional radiation 142. Accordingly, in this example a larger proportion of the radiation 142 is reflected to the measuring device. As a collimator of this kind, all systems used in the optics can be applied, such as an aperture plate and/or corresponding lens systems.

FIG. 4 illustrates another embodiment of the method according to the invention. The radiation 141 from the radiation source 15 in the form of a light source passes, via a semipermeable mirror 17, into the measuring axis 19 of the measuring device 16 in the form of an infrared sensor and is projected onto the surface 10, the reflected radiation passing to the measuring device 16 together with the natural surface radiation 13 of the body 11. Incident radiation and outgoing radiation are in the same direction with regard to the surface 10 and are also focussed by the optics 18. One particular advantage in this case is also the fact that the light source 15 and the measuring device 16 are combined in a common and compact apparatus 100 which is mounted outside the furnace wall or on the periphery of the furnace wall such that it can be rotated in at least one direction, with the result that the beam path 13 can be moved to an area of the surface 10 that is optimum for measurement, such that it is for example possible to monitor a reaction taking place in the furnace through a window only. The Figure also shows the effect of a local deviation of the topography of the surface 10, i.e. the beam 142 arriving at the surface is reflected off the surface 10 at the inclined edge of the crater 101 in the form of the beam 131. In contrast hereto, the beam 132 is not reflected off due to a local deviation of the topography, but due to the fact that it originates from a beam 141a of the radiation source 15, which diverges too strongly.

Figure 4A:
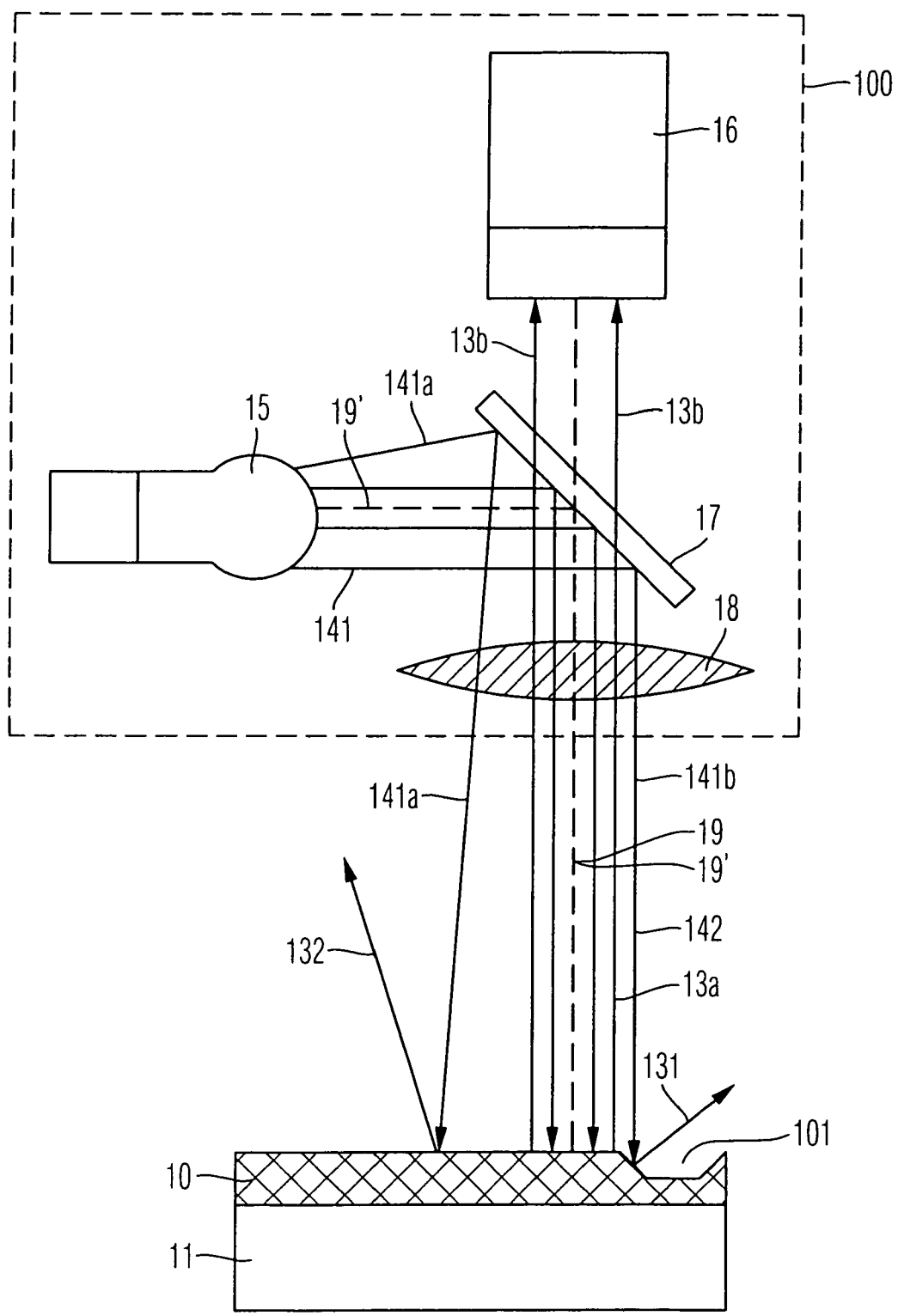
FIG. 4a shows a diagrammatic illustration of a modification of the second embodiment of the method according to the invention, and the direct radiation of the radiation source (15) on the surface (10) by using a semipermeable mirror (17)
Figure 4B:
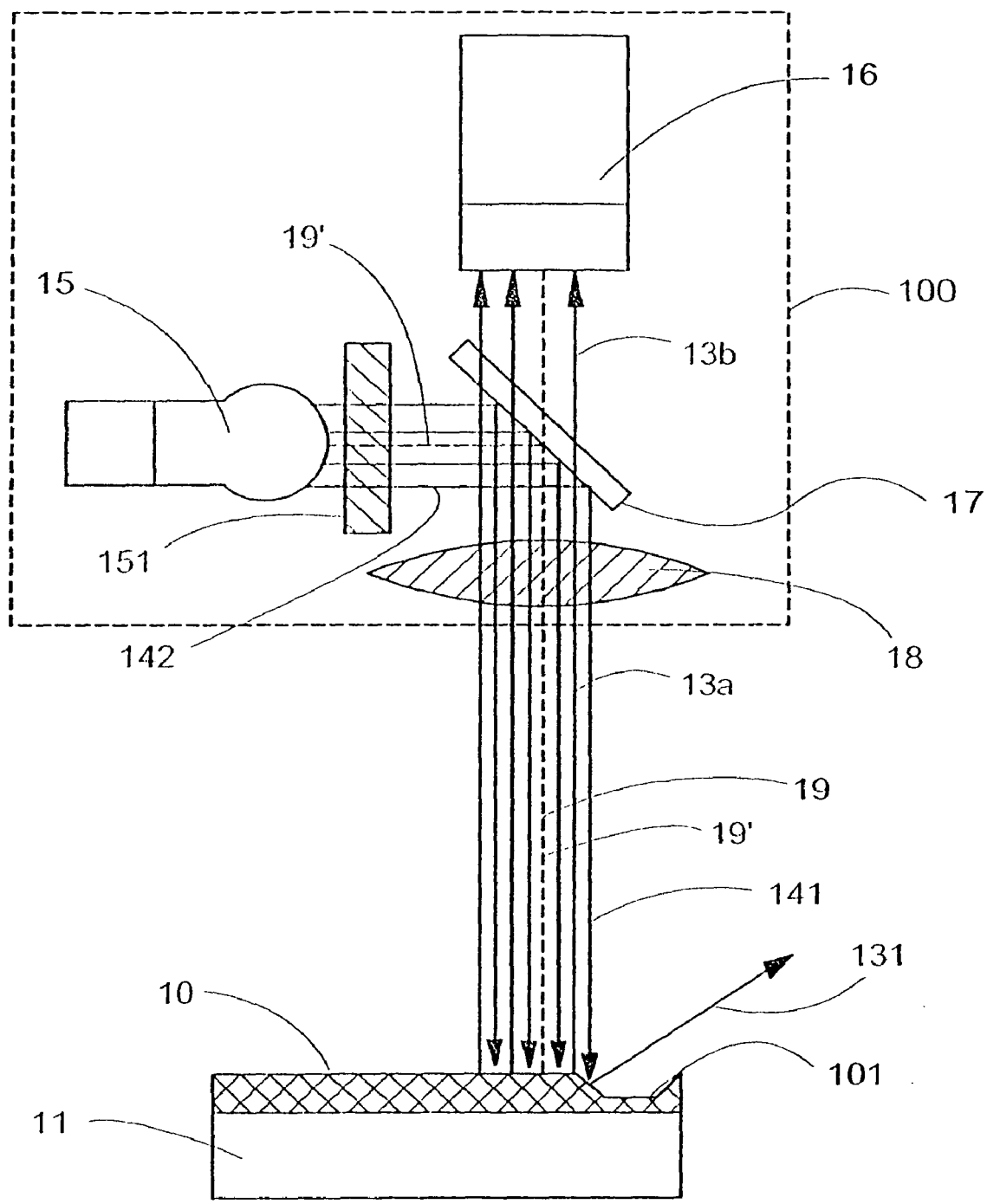
FIG. 4b shows a diagrammatic illustration of a modification of the second embodiment of the method according to the invention that uses a collimator (151)

FIG. 4b shows the same exemplary embodiment as FIG. 4a, but using a collimator which bundles or concentrates the radiation of the radiation source 15. For this reason, in this case only beams are reflected off the detector which are—like the beam 131—influenced by local deviations 101 of the surface 10.

Figure 5:
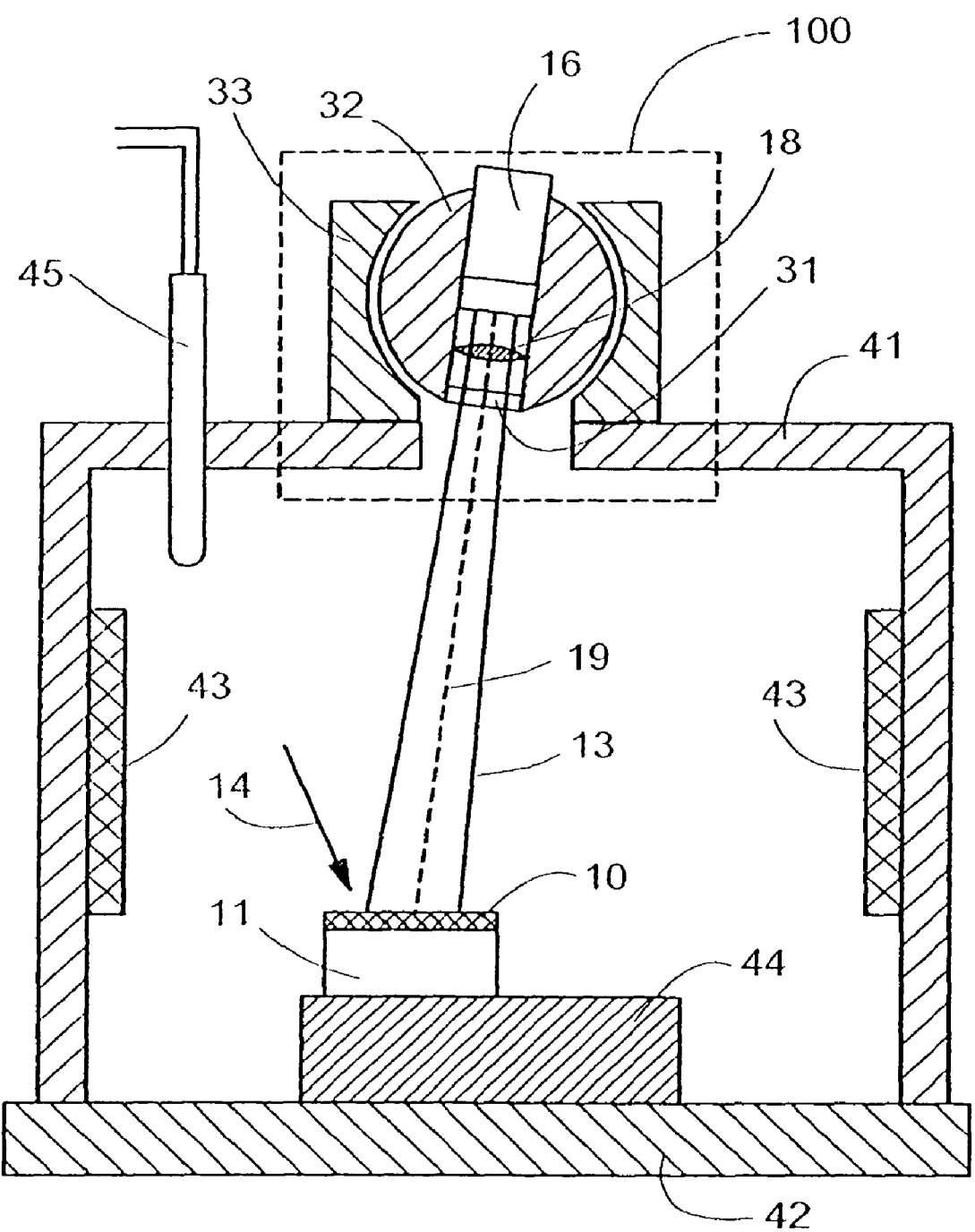
FIG. 5 shows a diagrammatic illustration of a third embodiment of the method according to the invention comprising a mobile detector unit.

FIG. 5 shows an apparatus according to an alternative of the first embodiment of the method according to the invention, said apparatus being mounted on the bell-shaped cover 41 of a furnace which is sealed against the furnace base 42 by means of a flange (not shown). The surface 10 of the body 11 is situated in a slightly offset manner toward the central axis of the furnace on a ceramic carrier material 44 in the lower area of the furnace and is heated by a heating element 43 which is fastened to the wall in the form of a jacket. This is an arrangement which is typically found in the furnaces for firing dental ceramic and the body 11 can therefore also be interpreted below as being a stylized partial surface of a dental firing object. The temperature of such furnaces is generally controlled using a thermocouple 45 which, for design reasons, is generally arranged far away from the body 11, for example close to the upper furnace wall.

Since heating is effected in a very short period of time using a heating element 43 which is cylindrically extended over part of the lateral surface of the furnace, the temperature detected at the thermocouple 45 is only indirectly related to the temperature which effectively exists at the body 11 at the time, and an exact time/temperature curve for ensuring firing success can be maid only with the aid of empirically determined correlation function between the display of the thermocouple and the effective temperature of the body 11. However, in the sense of the method according to the invention, this thermal disequilibrium is an advantage since the strong irradiation of the surface 10 by the heating element 43 which surrounds it allows good selectivity when determining the discontinuities in the radiation intensity curve, as is diagrammatically shown in FIG. 2, with the result that that method variant which manages only with the natural radiation of the object and without an extraneous light source 15 can be selected.

Dental objects naturally are of small dimension and it is important in this case for the firing process to be monitored at desired locations of their surface. The detector 16 and the lens system 18 must therefore be selected in such a manner that they allow an only small surface area of the surface 10, for example a diameter of 1-2 mm, to be monitored over the measuring distance. In order to make it possible measure a particular area in an exact manner, the apparatus 100 in this exemplary embodiment comprises a vacuum-tight housing 31 in which the lens system 18 and, in the front area, a vacuum-tight window 34 are also situated.

The housing 31 is mounted inside a ball body which can generally be moved using a seal (not illustrated) in the housing 33. For its part, the housing 31 is tightly connected to the furnace cover 41. Such an arrangement is also suitable for the variants of the method according to the invention in which an additional radiation source 15 is used; this applies especially to the compact apparatus which is shown in FIGS. 4*a* and 4*b* and in which the detector 16 and the radiation source 15 have a common optical axis 19 with a semi-transparent mirror 17.

In order to position the optical system exactly, two methods which are conventional in infrared measurement can be used. One possibility is to use a laser whose light spot allows exact positioning. Known IR detectors which already contain such a laser positioning lamp are suitable for this purpose. Alternatively, the operator can view the image field of the sensor 16 through an eyepiece which reflects light in laterally. There are also embodiments in which the eyepiece is replaced with a video camera, with the result that the image field can be comfortably viewed on a monitor.

In the exemplary embodiment illustrated, the body 11 is, for the rest, situated at the bottom of the furnace chamber such that it is slightly shifted to the left, with the result that the optical axis 19 of the sensor 16 is slightly inclined toward the vertical. Unlike the design illustrated here, the actual detector may also, of course, be permanently mounted at a location outside the furnace wall and it receives its information via a glass fiber bundle whose front part is mounted in a ball 32 in a vacuum-tight manner analogously to the arrangement shown in FIG. 5. It goes without saying that, in all of these arrangements, it is necessary for all of the optical elements through which the beam 13 passes, that is to say the lens system 18, the window 34 and, if appropriate, a glass fiber line, to comprise a material which transmits the selected wavelength.

In the exemplary embodiment illustrated, the apparatus 100 can be moved in all spatial directions using a ball 32. In a manner matched to the measurement problem, other possible movements can also, of course, be selected; an apparatus which allows movement only in one axis suffices in many cases.

However, the aim of exactly positioning the measuring spot can also be achieved in a simple manner by permanently mounting the detector 16 in accordance with FIG. 1 and the combination of the detector 16 and the radiation source 15 on the periphery of the furnace wall or outside the furnace wall and by optionally sighting the furnace chamber through an opening which is provided with a sealed window, the body 11 being positioned on a holder which can be moved or rotated in at least one spatial direction. This makes it possible to approach the desired area of the surface 10 by appropriately moving a displacement or rotating mechanism in one or more axes.

The above-described possibility of displacing the body 11 can not only be used to exactly position the measurement object inside the surface 10 but also allows a larger area of the surface to be simultaneously monitored. For this purpose, the body is moved periodically, the optical measurement being carried out in a clocked manner during this movement, and the values which are respectively ascertained at the same location forming the intensity function of this area of the surface 10 and being individually evaluated in accordance with the diagram shown in FIG. 2. Corresponding software run by a computer processor can then determine, for example, at which location of the surface 10 a chemical and/or physical process begins or at which location it finally ends.

Whereas the exemplary shown in FIG. 5 shows permanent installation in a furnace for a specific purpose, for example for monitoring a dental firing process, the method according to the invention can be used to monitor any desired processes using a quotient pyrometer, as are usually used for the purposes of measuring temperature. As described at the outset, such pyrometers measure for two wavelengths; this may be effected by simultaneously using two detectors or else using one detector which has two corresponding optical filters which respectively allow only a particular wavelength range to pass. Such a pyrometer usually provides a channel which converts the radiation density of one of the two wavelengths into a "black temperature", a value, which must be corrected, if necessary, by inputting an emissivity. The second channel generally provides the temperature which is calculated from the intensity ratio of the two wavelengths and is normally close to the effective temperature of the measurement object.

In the sense of claim 17, such a measuring device can be used in accordance with the method according to the invention to monitor physical and/or chemical processes by evaluating the temporal profile of the intensity curve or else of the temperature value of a wavelength—it runs practically parallel to the intensity—with respect to the discontinuities in accordance with procedure shown in FIG. 2. However, a particularly elegant method also results if the temperature value of a wavelength is subtracted from the temperature value of the quotient channel, in which case, instead of the functions themselves, their first derivatives may also be used. The differential value can then be optionally integrated again. Even the slightest discontinuities which are not attributed to a change in temperature but rather to a change of the emission behavior can be rendered visible by this method. Such a quotient pyrometer can optionally also have a relay which carries out a switching operation when a particular change in the emission behavior occurs in order to thus trigger an alarm, for example, or to control a furnace. In cases of radiation equilibrium, the light from a radiation source 15 may also, of course, be projected onto the measurement object in the sense of claim 2 and FIG. 3, this radiation source either being able to be part of the pyrometer, that is to say its light is passed into the optical axis of the pyrometer via a semipermeable mirror, or else being able to be separately fitted inside or outside the furnace chamber.

Figure 6:
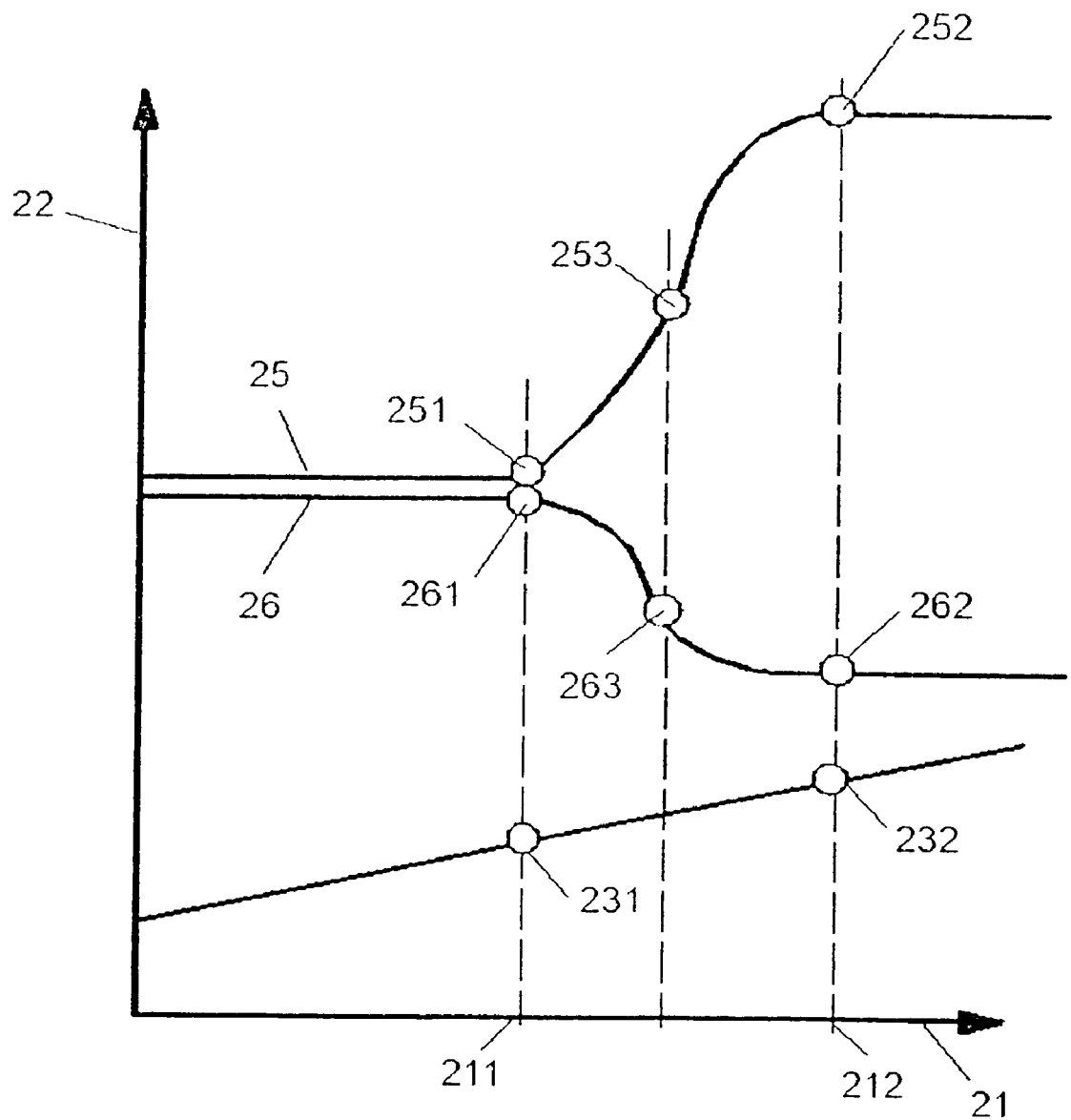
FIG. 6 shows a diagrammatic illustration of the temporal profile of the radiation intensity of a surface in the course of a heating process in a furnace according to FIG. 3a to 3c, during which a chemical and/or physical transformation takes place at a particular point in time.

FIG. 6 shows—in an analogous manner to FIG. 2a—a diagram of the radiation 13 reaching the measuring device 16, said radiation being influenced by the extraneous radiation 141 emanating from the radiation source 15. Since the radiation 141 is arranged in a completely different wavelength range of the spectrum, e.g. the range of blue light, and the detector of the measuring device 16 also operates in this wavelength range and possibly is even protected against longer-wave thermal radiation of the furnace by means of a filter connected upstream of the furnace, the curves 25 and 26 run completely horizontal before the beginning of a reaction and correspond to the proportion of the radiation 141 which is reflected from the surface 10 to the detector.

Also in this case, it is also assumed that a sintering process takes place, i.e. at the beginning the unsintered surface 10 comprises a strong throwing power, such that the detector is exposed to a diffuse medium irradiation. With the beginning of the sintering process the surface 10 begins to smooth increasingly, which results in a decrease of the spreading, i.e. an increasing dependancy on the local inclination of the surface 10 follows. With the curve 25 it is assumed that more and more radiation 13 that becomes increasingly more intensive on account of the decrease of the spreading effect reaches the detector, resulting in a rise from point 251 up to point 252 at which the sintering process terminates and a completely smooth and reflecting surface has formed.

Contrary to this, with regard to the curve 26 it is the case that—due to the relative position of the detector 16 with respect to the angle of incidence of the extraneous radiation 141 originating from the radiation source 15—the radiation 13 is increasingly reflected past the detector, with the result that an increasing decrease of the radiation intensity from the beginning of the sintering process at the point 261 to its end at the point 262 takes place.

The curve 23 shows again the profile of the temperature or 231 and 232 the temperatures at the beginning and the end of the sintering process, respectively, whereas in this case this temperature, however, has to be determined by a completely independent method for temperature measurement.

The curves shown in FIG. 6 clearly show the advantages of the second embodiment of the method according to the invention by using an independent radiation source 15 having a radiation spectrum differing from the temperature of the surface 10. The actual measurement event, i.e. the discontinuity caused by a physical and/or chemical process, becomes significantly more apparent since it originates from a curve that runs horizontally and does not—as a more or less weak event—superimpose a curve that is particularly characterized by temperature changes. For this reason, in many cases the beginning and the end of a reaction can be determined directly from the measurement curve itself and do not have to be ascertained by using the first or second derivative according to FIGS. 2b and 2c.

As shown in the curves 25 and 26, one and the same sintering process as a function of the angle position of the monitored surface with respect to the detector is represented in very different ways. If the position of the surface is arranged in a way that a large portion of the reflected radiation reaches the detector, the rising curve 25 having a large amplitude will result, whereas in the case that a large portion of the radiation is reflected off the detector, a falling curve having a lower amplitude will be the result. This variety of measurement situations does not play a role if a detector measures a specimen with a reproducible geometry, e.g. with a smooth surface, said specimen always being located at the same position. As a function of the execution of the physical and/or chemical process, e.g. a sintering process, always the same curve will arise for the same material, that is to say there is the possibility to work with a fixed calibration factor. Things are, however, significantly more complex, if e.g. a sintering process with an arbitrarily shaped body such as in the case of a dental firing object, is to be monitored by means of a plurality of detectors that are arranged in a pixel matrix, e.g. a video camera. Each of the pixels represents a different area of the surface having an individual local inclination, that is to say each of the pixels for this reason has an individual calibration factor for this curve as can be seen from the different amplitudes of the curves 25 and 26.

If the sintering progress, however, were to be evaluated on a total surface with a complex surface topography in a uniform manner, it is necessary to unitize the plurality of these curves. Due to numerous sintering experiments, the following evaluation method could be developed by means of which the following standardization is possible:

Both the curve 25 and the curve 26 comprise an inflection tangent at the positions 253 or 263, respectively, which manifest themselves as maximum or minimum of the sintering function in the first derivative and can be determined by a simple algorithm; the same also applies to the beginning of the sintering process at the points 251 or 261, respectively, said points being defined by zero points of the first derivative. From a physical point of view, the beginning of the sintering curve implies a first-time change of the surface of the test specimen e.g. the formation of first sintering necks at energetically particularly favorable contact points of adjacent grains under the influence of the low-activatable surface diffusion.

Even the inflection tangent of the curve exhibits physical importance, since for a particular material it represents a reproducible intermediate state from the beginning of the sintering process to the moment when the sintering process has been completed. Numerous experiments have shown that the point of the inflection tangent approximately corresponds to the state in which the sintering necks have disappeared and the individual particles coagulate to larger compounds by eliminating the open porosity, that is to say a moment which is also characterized by the transition from surface diffusion to volume diffusion.

The alteration of the detector signal from the beginning of the sintering process to the point of the inflection tangent can thus be used for a specific material as a reference distance for the assessment of the entire sintering curve. The fact that a defined assessment of the sintering curve is not possible before the occurrence of its inflection point, is not of interest in this case since this first section of the sintering curve is absolutely irrelevant for the final quality of the firing process; this quality is achieved only in the following second section of the sintering curve in immediate vicinity to the ending point, e.g. with reference to the curves 25 and 26 at the points 252 and 262. In this area the curves already run very flat and the point of optimum sintering can be defined by a critical gradient of the curve that has been determined empirically. In this moment it is, of course, obvious that the same critical sintering state near the point 252 is represented by a larger gradient as it is the case for the curve 26 in the same proximity to the end point 262, which also even has the opposite algebraic sign. In order to achieve a unitized or standardized gradient $a_{norm}$ the following formula has been implemented:

$$a_{norm} = \frac{a_{25}}{(P_{253} - P_{251})} = \frac{a_{26}}{(P_{263} - P_{261})}$$

Thus, each gradient a of the curves 25 and 26 after the inflection tangent points 253 or 263, respectively, can be standardized by dividing it by the alteration of the measured value between the beginning and the inflection point of the curve; this also applies to the algebraic sign since both the value $a_{26}$ and the difference ($P_{263}$-$P_{261}$) are negative in the example of FIG. 6, and thus, the standardized gradient in the form of the quotient also obtains a positive algebraic sign like the corresponding quotient of the curve 25.

With this method it was made possible to control a dental firing furnace without the aid of an exact firing temperature, whereas a plurality of different dental firing compounds with most-different firing temperatures and firing times were employed. The furnace raised the temperature in a first phase using a fixed heating velocity until the beginning of the sintering process became apparent by a significant deviation of the first derivative of the curve from the zero point. The values of all pixels were saved at this point in time and then it was waited until the moment of the inflection tangent which manifested itself by the occurrence of a maximum or minimum in the curve of each pixel. From this moment on, the above formula was implemented and it could be seen that the curves of all pixels virtually coincided. This point in time was also used for reducing the furnace power.

Such an ideal behavior of course only occurs if the sintering process takes place simultaneously in the whole surface monitored. In practice, however, this is never the case, since on the one hand, the temperature field in a small dental furnace is not homogeneous and, on the other hand, the sintering process locally takes place faster at sharp edges as a result of the influence of the surface tension. The evaluation method represented above thus is of even greater importance, since the local sintering progress at each position of the firing batch can be evaluated uniformly by means of it. In order to achieve an optimum firing result, for example an algorithm can be selected where a minimum number of the changing pixels has reached a given standardized final gradient by means of which it is assured that even unfavorable positions of the firing batch are sintered to the optimum point. This is only an example for a controlling process which is especially suitable for dental firing processes, whereas for other processes, e.g. for monitoring the alteration of the stoichiometry of surface oxides of metals when changing the temperature and/or the oxygen partial pressure, however, a plurality of other algorithms are conceivable, but which usually also corresponds to an individual adaption to the individual form of the first derivative of the detector curves of these processes, in particular by using maxima, minima and zero points.

Figure 7A:
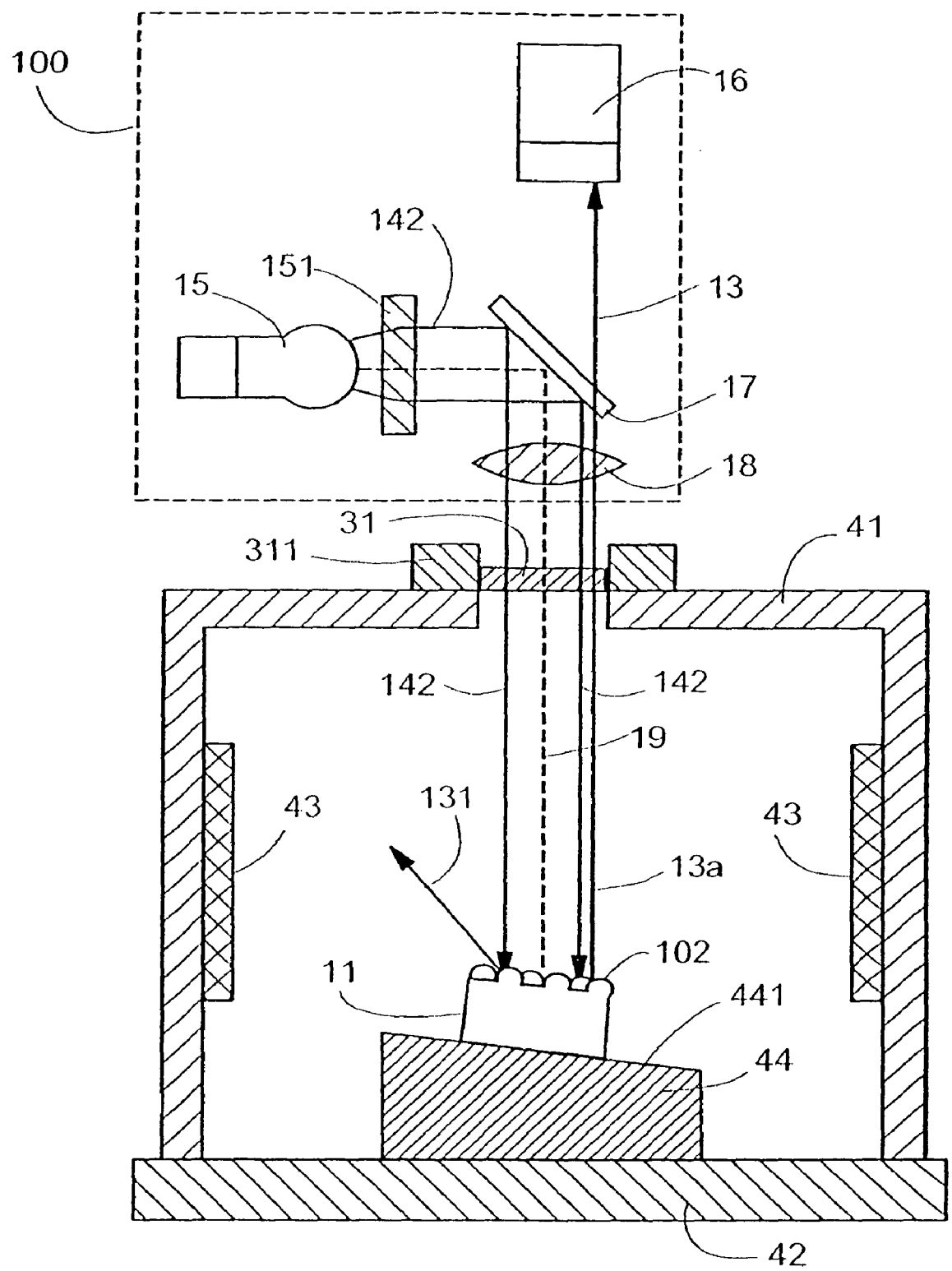
FIG. 7a shows a diagrammatic illustration of a modification of the second embodiment of the method according to the invention at the beginning of a sintering process.

FIG. 7a shows an arrangement similar to the arrangement shown in FIG. 4b, which is particularly suitable for monitoring the sintering process of ceramic or metal green bodies having a smooth surface. The body 11 with its still unsintered surface 102, which is schematically represented as an accumulation of spheres, is situated on a sample carrier 44 having a surface 441 that is inclined towards the horizontal in a specific angle, in the center of the optical axis 19 of an optical system 100. The strong spreading effect of the surface is represented by a directional beam 142, whose reflection 131 is being reflected off the detector 16, while another beam 142 strikes a part of the surface. The reflection 13a of the beam passes through the semipermeable mirror 17 and directly enters the detector through the lens system 18 in a slightly attenuated manner as radiation 13b. Due to the fact that the detector 16 is only sensitive in the wavelength range of the radiation source 15, neither the natural thermal radiation of the surface 102 nor the reflected portion of the radiation of the heating coils 43 can be detected. The semipermeable mirror 17 allows both the incident and the reflected radiation to be guided through a window 31 that is arranged in the vacuum-tight flange 311, said window preferably consisting of silica glass, as a result of which the opening in the furnace chamber can be kept as small as possible.

Figure 7B:
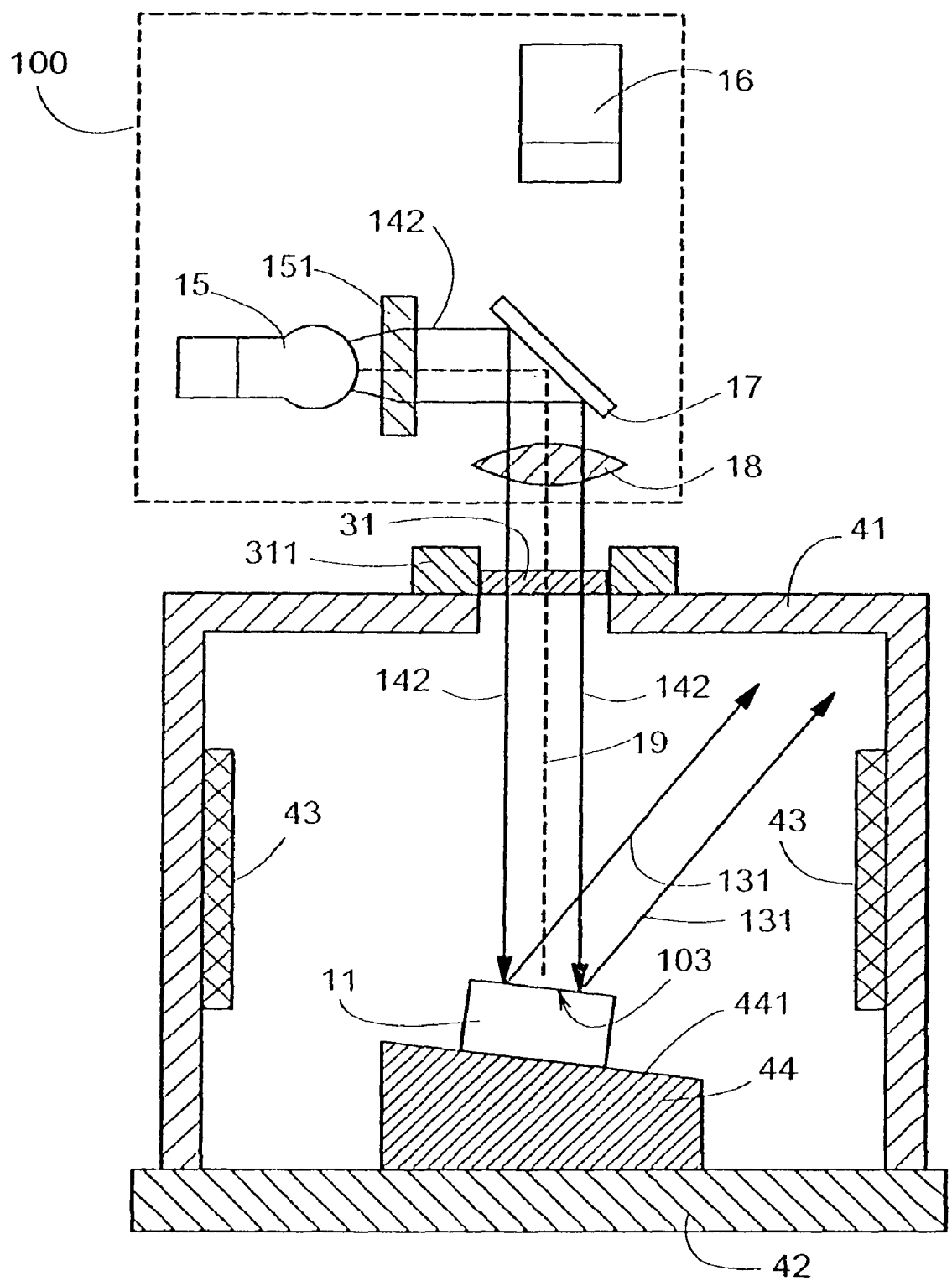
FIG. 7b shows a diagrammatic illustration of a modification of the second embodiment of the method according to the invention at the end of a sintering process.

FIG. 7b shows the advantages of such an embodiment using the test specimen table 44 with the inclined surface 441. The angle of this inclination was selected such that the surface 103 smoothened by a sintering process cannot send a shiny reflection to the detector 16, which might be the case if the body 11 were to lie on a horizontal table. Due to the fact that beams reflected from a glassy surface exhibit an extremely tight spreading cone, even the slightest deviation from the horizontal would result in partial areas of the surface 103 either appearing completely dark or showing extremely shiny reflections, whereas according to FIG. 6—purely by chance—either the characteristic of curve 25 or of curve 26 forms. Due to the inclination, however, the behavior always clearly corresponds to curve 26 of FIG. 6, that is to say in the unfired state, a medium radiation intensity will be the result that can decline to nearly zero during the sintering process, as it is schematically shown by the two beams 131 that are strongly reflected off the optical axis 19.

Figure 8A:
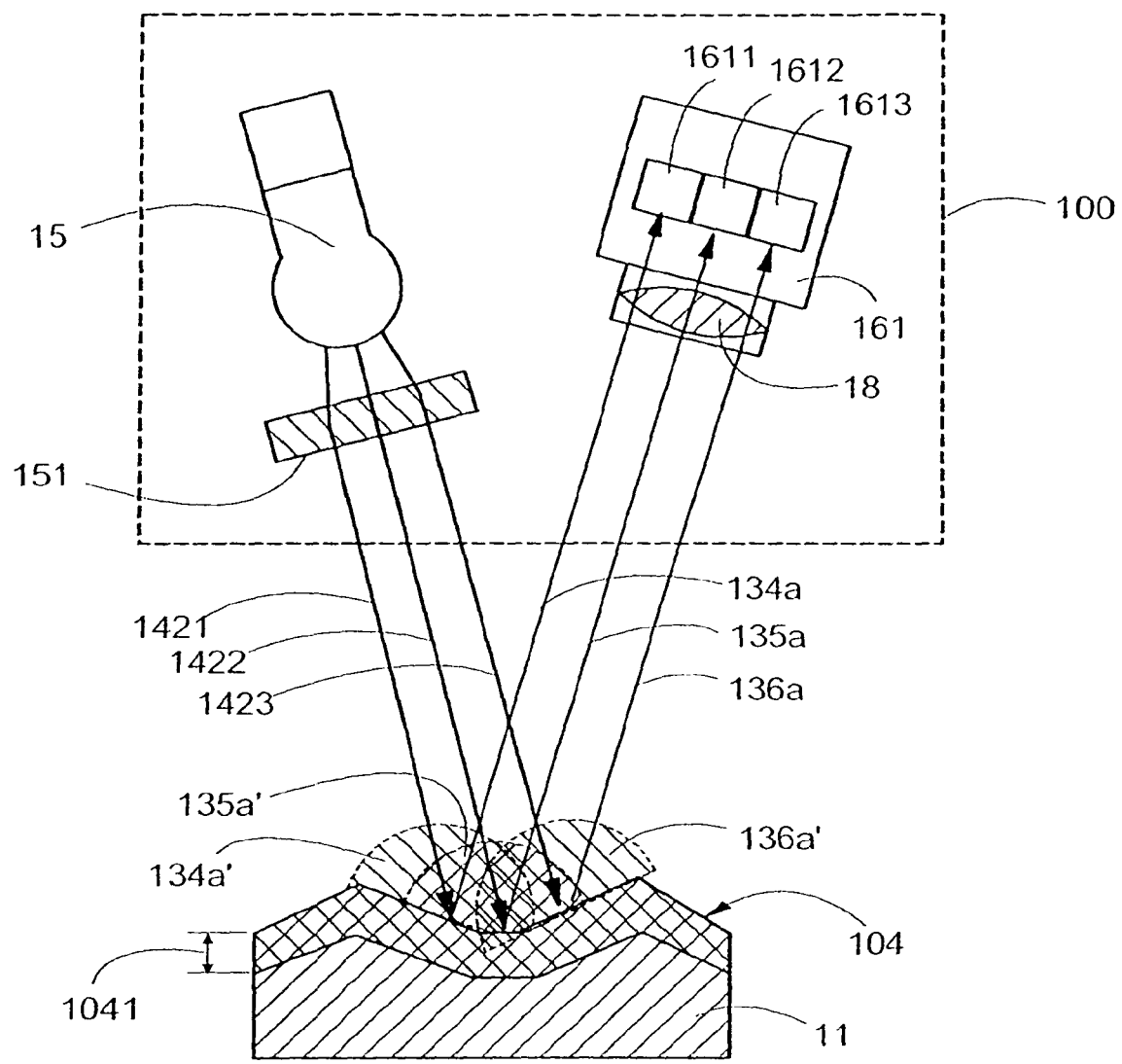
FIG. 8a shows a diagrammatic illustration of a modification of the second embodiment of the method according to the invention, comprising several detectors arranged as a pixel matrix on a surface that initially has a high roughness depth.

FIG. 8a shows an alternative of the second embodiment of the method according to the invention, using a radiation source 15, whereas, however, according to the teachings of claim 8, a matrix of sensors instead of a single detector is used, said matrix being shown in a schematically highly simplified manner by the three sensors 1611, 1612 and 1613, which are part of a device 161 having a matrix. As a device of this kind, for example, a sensor matrix as it is also used in digital cameras, video cameras and e.g. UV cameras, can be taken into consideration, whereas in this case the radiation source 15 also needs to work in this range. However, it is possible to use a conventional video camera that illuminates a measuring object, e.g. with a radiation source 15 in the blue light range, whereas this camera only uses this short-wave range for the measurement. This may, e.g., happen by the incident radiation 13 passing an optical filter on its way to the sensor matrix 161, which filter eliminates the long-wave range, or it may, however, also happen on the level of evaluation by evaluating only the long-wave portions of the video signal.

In order to obtain a light yield as large as possible, this method alternative works without a semipermeable mirror, that is to say the radiation source 15 with collimator 151 as well as camera 161 with its lens system 18 have their own optical axes which are angled against each other, and interface on the surface 104 of the body 11. In the present example the influence of the spreading that is caused in the microarea by the roughness depth 1041 of the surface 104 irrespective of its local alignment, is intended to be clearly delimited from the effect of the alignment of partial areas in the macroscopic range. This would, for instance, correspond to the surface of a ceramic green body, whose surface provides partial areas that are strongly inclined against each other, as it is typically the case with dental firing batches for example.

In this schematic representation, the radiation source 15 emits three beams 1421, 1422 and 1423 that strike different inclined areas of the surface 104, but each of these beams have the same degree of roughness and thus the same spreading effect. As a result of this large spreading effect the hemispherical spreading balls 134a', 135a' and 136a' are generated, which are supposed to symbolize that all partial areas—regardless of their local inclination—radiate in roughly the same manner and uniformly in all spatial directions. Thus, each of the pixels 1611, 1612 and 1613 of the detector matrix 161 receives a small portion of the radiation in the form of the reflected beams 134a, 135a and 136a, which manifests itself in the fact that the detector matrix is illuminated uniformly to a large extent and without major contrasts.

Figure 8B:
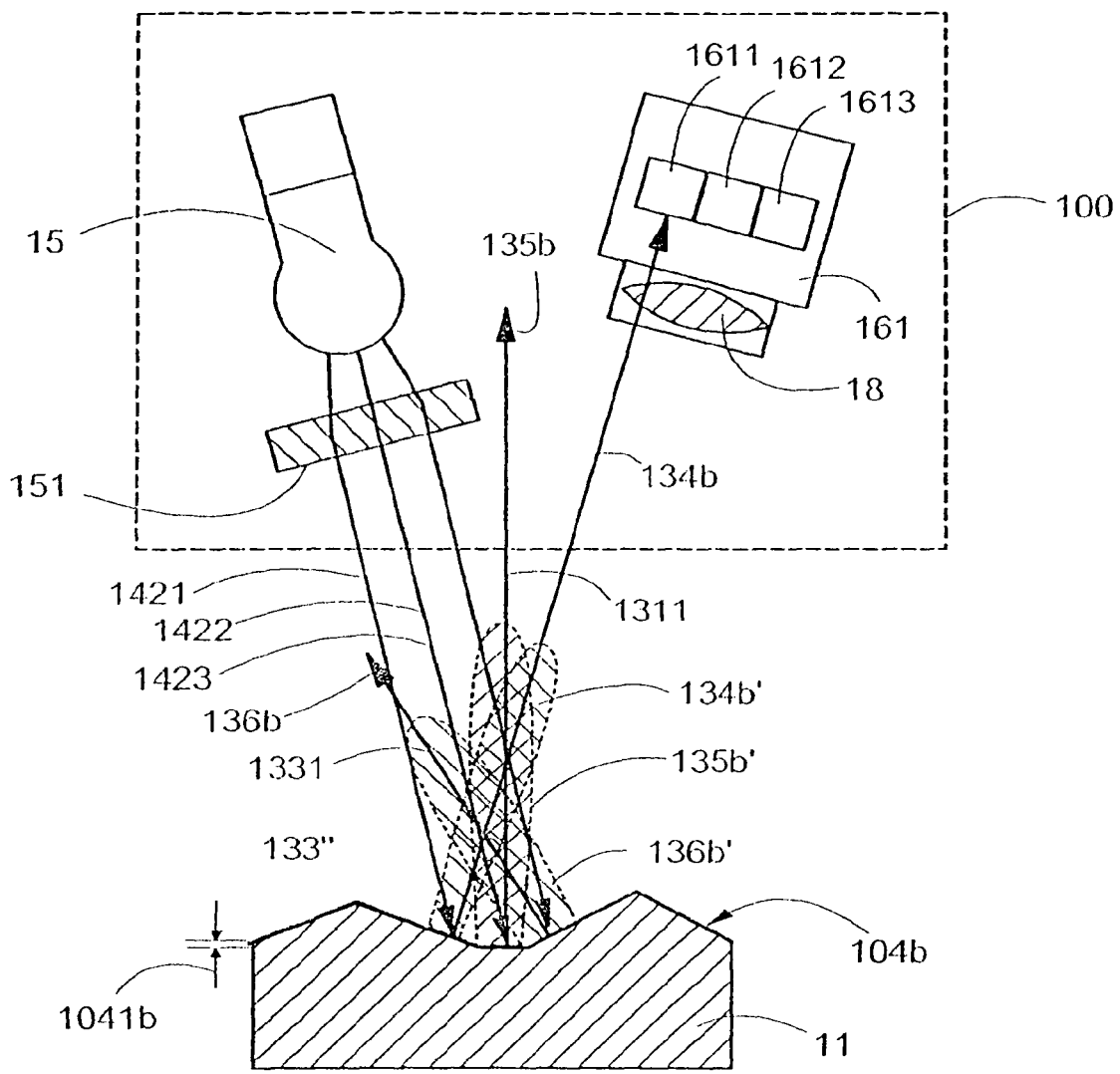
FIG. 8b shows a diagrammatic illustration of the embodiment according to FIG. 8a having a reduced roughness depth of the surface.

FIG. 8b shows a transition of a reaction which has started in the meantime, where the macro-relief structure of the surface 104b still corresponds to the state for the surface 104 shown in FIG. 8a, but the roughness depth, however, has declined to the value 1041b. For this reason, the width of the spreading cones 134b', 135b' and 136b' has also decreased. The spreading cones are now situated closer at the direction that corresponds to the direction of incidence of the beams 1421, 1422, 1433 along the perpendicular bisector of the side of the respective partial area irradiated, the beams being reflected off in the inverse direction. The tighter spreading cones result in a higher radiance or beam density but only the partial area that was irradiated by the beam 1421 has exactly the angle of inclination that directs the reflected beam 134b to the pixel 1611 of the detector matrix 161, and the beams 135b and 136b are reflected off the detector. Thus, in this phase of the reaction the result is an increase of the radiation intensity at the detector pixel 1611, while the pixels 1612 and 1613 show a decreasing radiation intensity.

Figure 8C:
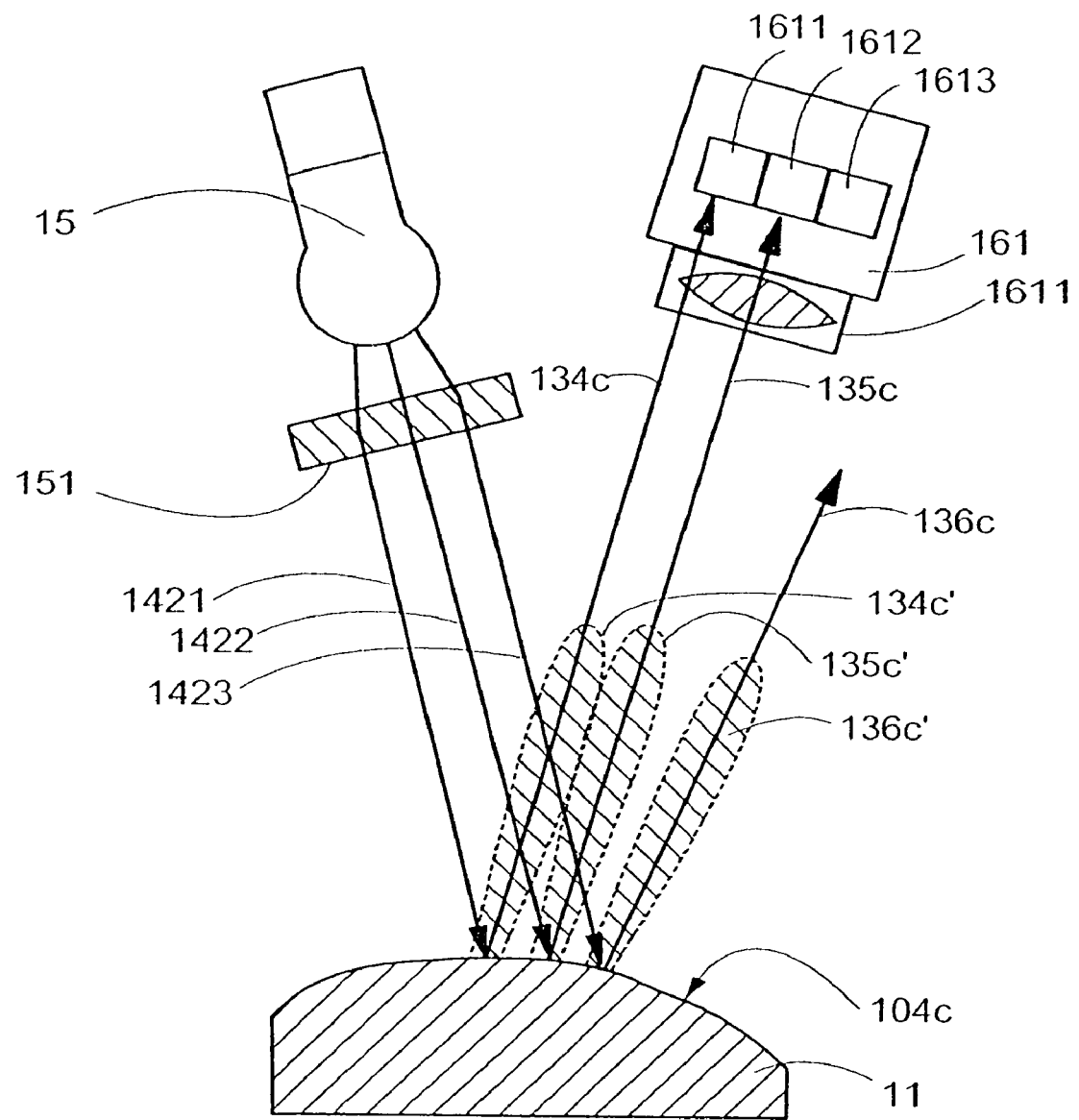
FIG. 8c shows a diagrammatic illustration of the embodiment according to FIG. 8a comprising a surface that is smooth and increasingly plane under the influence of surface tension.

FIG. 8c shows the final state of the reaction, whose transition was shown in FIG. 8b. Under the influence of the surface tension that is extremely expressed e.g. in the last stage of a firing process due to the high flexibility of the firing batch, the surface which used to consist of different inclined partial areas changed to the roundishly bossed surface 104c, which has a high reflectivity. Large parts of the surface now have an approximately similar inclination, so that the reflected radiation portions 134c and 135c that originate from the directional beams 1421 and 1422, now reach the pixels 1611 and 1612 of the detector matrix 161, while only the beam 136c aims past the detector due to the low local inclination of the surface 104c. Since the spreading cones 134c', 135c' and 136c' have narrowed—compared to FIG. 8b—even a bit more, the radiance both of the beams striking the detector pixels and those beams missing them, has increased.

Figure 8D:
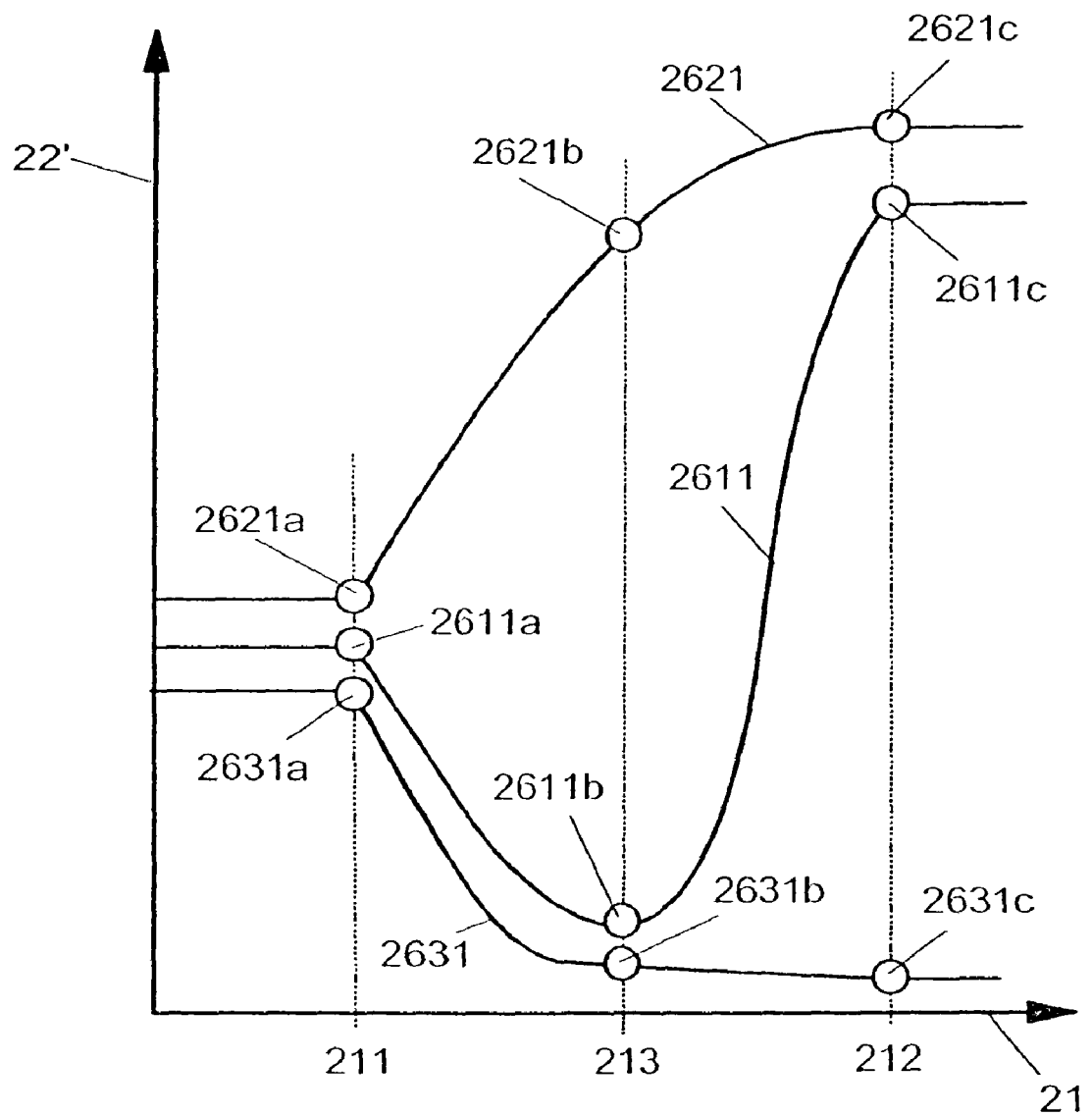
FIG. 8d shows a diagrammatic illustration of the intensity curves of the detectors of a pixel matrix during the changes in the surface according to FIG. 8a to 8c.

FIG. 8d shows in summary the radiation intensity functions of the three pixels 1611, 1612 and 1613 as illustrated schematically in the FIG. 8a-8c during different stages at the points in time 211, 212 and 213 of a reaction, e.g. of a sintering process. Before the start of the reaction, the radiation intensity detected by each of the three pixels is very similar due to the strong spreading effect, that is to say the starting points 2611a, 2621a and 2631a of the reaction are close to each other. Subsequently, however, according to the different alignments of the partial areas, beginning at the initial condition of the surface 104 to final condition of the surface 8c, a different behavior develops for each of the pixels.

In case of the pixel 1611, the radiation intensity decreases due to the decreasing spreading effect and the inclination of the surface pointing away from the detector—from the point 2611a towards the intermediate state of the reaction to the value 2611b, whereas in the last state of the reaction the surface, however, smoothens, such that the measured value of the pixel 1611 increases up to the final value 2611c.

In the case of the pixel 1621, which is a part of the surface and always aligned advantageously relative to it during all phases of the reaction, the increasing decrease of the roughness depth results in a continuous increase of the radiation intensity according to the values 2621a via the value 2121b to the final value 2121c.

The pixel 1631 also shows a constant behavior, in this case the partial area represented by said pixel is always inclined towards it in such an angle that the radiation is always reflected off; under the influence of the decreasing spreading effect this effect is becoming stronger and stronger, so that the radiation intensity is continuously decreasing beginning with the initial value 2631a via the intermediate state 2631b to the final state 2631c.

The method alternative described in FIG. 8a-8d works according to the second embodiment of the method according to the invention, i.e. using a radiation source 15, which preferably operates in a wavelength range lying beyond the spectrum of the natural thermal radiation of the surface 10 and its surroundings. The teachings of claim 8 can, however, also readily be used in combination with the first embodiment of the method according to the invention in which the extraneous radiation of the surrounding area is used. In such a case e.g. a component can then be used as sensor matrix as it is used in thermography or, for example, also a video camera working in the visible range, whose wavelength range also reaches the range of IR in many cases. In all these cases the evaluation then has to be carried out analogously according to the operating method shown for a sensor in FIG. 2, i.e. the information concerning the progression of a physical and/or chemical process have to be determined as a discontinuity from the progression of the signal curve of each pixel of the matrix. However, such an operating method is also subject to the principle restriction that applies to alternatives of the method of the first embodiment, that is to say the temperature of the surface 10 and its surrounding area has to either remain constant during the measurement process or change in a continuous manner, so that a discontinuity caused by a process becomes clearly recognizable.

An exception within these alternatives of the first embodiment is represented by the case where the progression of a polymerization process that is triggered by UV light is monitored in the inventive sense. The illumination system in the form of an UV lamp can thereby be considered as part of the surrounding area emitting extraneous radiation 14 since the lamp primarily serves the purpose of polymerization, and thus, represents a system-immanent part of the surrounding area of the surface 10. The part of the UV radiation reflected to the single detector 16 or to a detector matrix 161, in the inventive sense can then be used to monitor the progression of the polymerization reaction and to minimize the duration of irradiation, however, always under the condition that the polymerization is accompanied by changes in the optical properties that can be detected by the measuring device 16.

Figure 9:
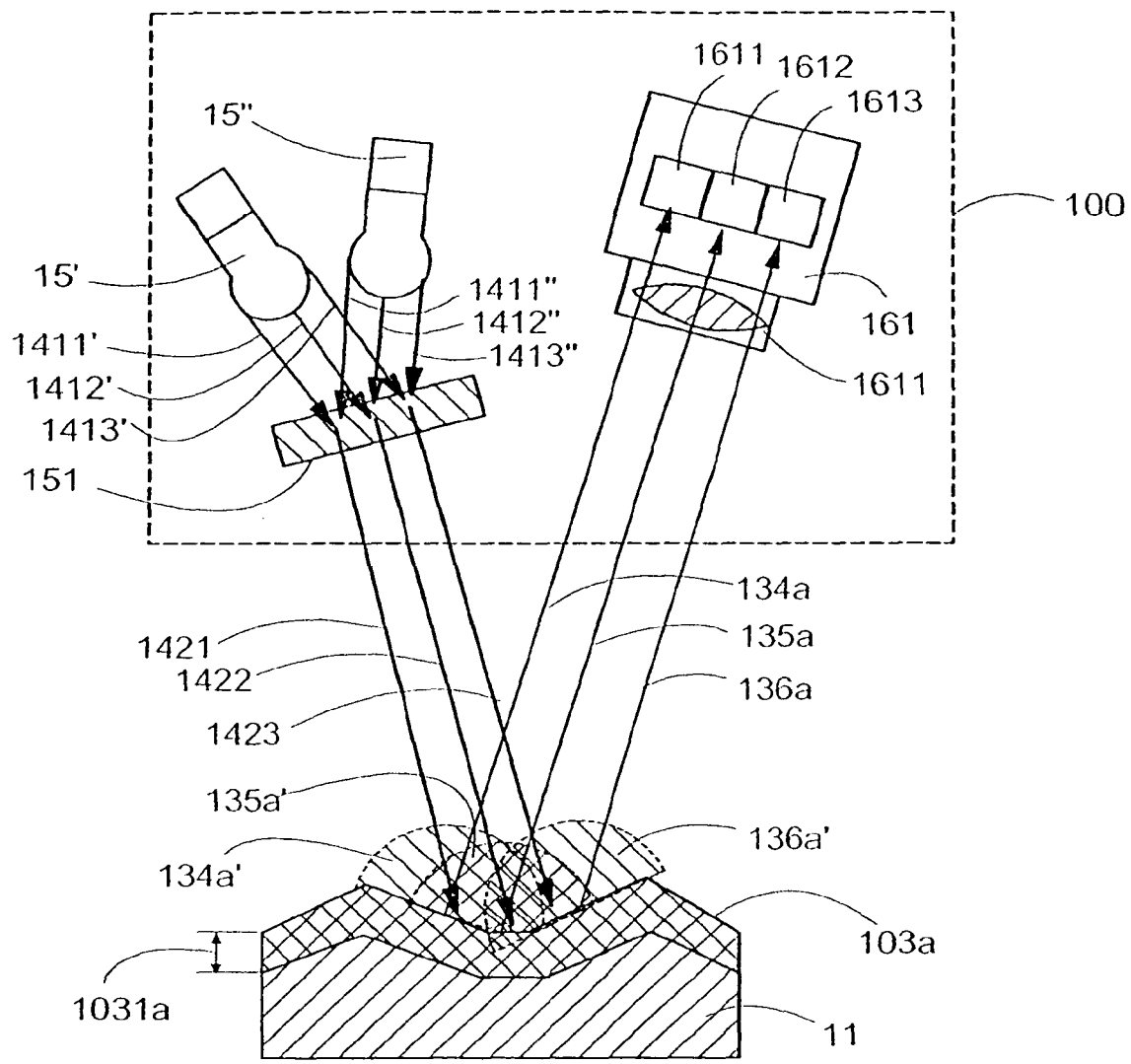
FIG. 9 shows a diagrammatic illustration of a modification of the second embodiment of the method according to the invention using two sources of radiation of different wavelength.

FIG. 9 shows another alternative of the second embodiment of the method according to the invention using two radiation sources 15' and 15" with different wavelengths, e.g. two UV LEDs, one of which operating in the wavelength range of 400 nm and the other operating in a wavelength range of 300 nm. The beams of both radiation sources are bundled or concentrated in a collimator and then projected as bundled or concentrated beams 1421, 1422 and 1423 onto the surface 104 of the body 11 where they—in an analogous manner to FIG. 8*a*—generate spreading circles corresponding to the roughness depth 1041 and the local surface relief, from which the reflected partial beams 134*a*, 135*a* and 136*a* reach the sensors 1611, 1612 and 1613 of the sensor matrix 161. The evaluation of the signals of these sensors is effected analogously to the illustration shown in FIG. 6, however, in duplicate manner by monitoring the progression of the radiation intensity both in the wavelength range of 400 nm and 300 nm.

In this case, the evaluation can be effected in two different manners. In the first case, the radiation sources 15' and 15" can be switched on and off by turns, so that for a short period of time only light of one of the two wavelengths reaches the sensor matrix, where its intensity is being measured. However, it is also possible that both radiation sources 15' and 15" operate at the same time, in which case the signals of the sensors of the matrix are then evaluated specifically in the range of the two wavelengths.

Instead of measuring the radiation intensity at the two wavelengths, however, the color value (e.g. the chrominance ratio of the signal) can also be measured apart from the radiation intensity (e.g. the luminance ratio of the signal), since every displacement of the intensity with the wavelength can also become noticeable due to a change in the color value.

Figure 10:
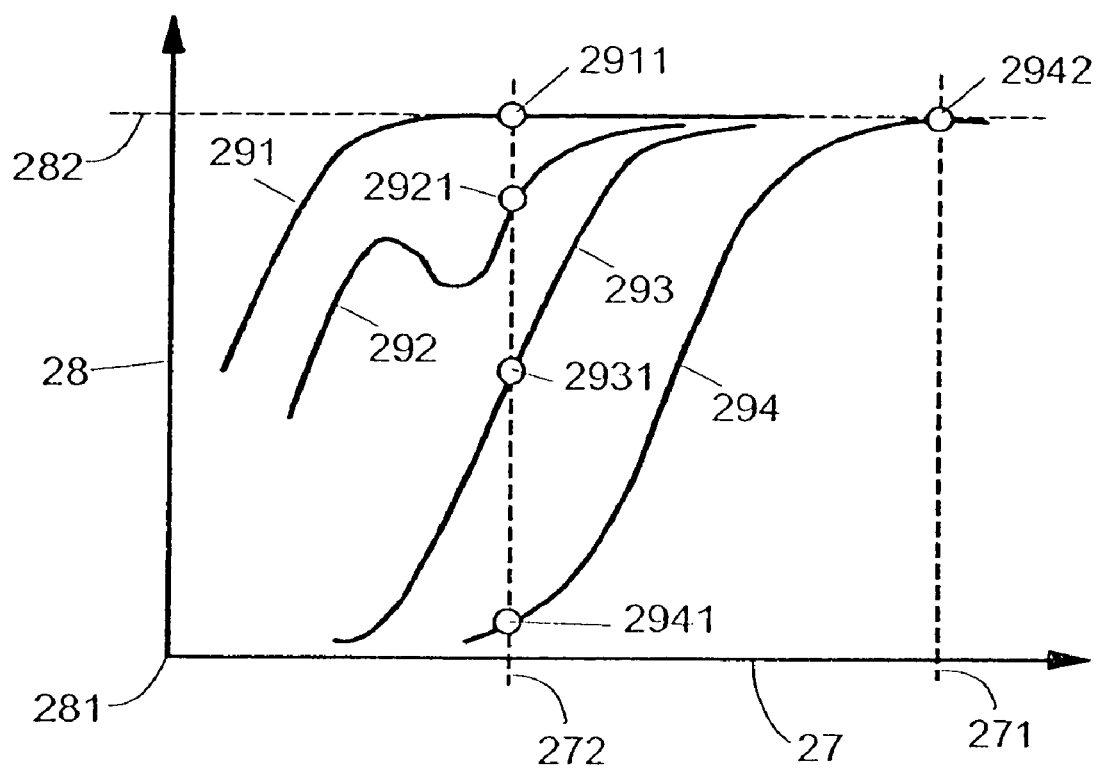
FIG. 10 shows the transmissivity of silica glass and silicates in the UV range as a function of the wavelength.

FIG. 10 shows the sense of such a measure specifically for monitoring the reactions with glasses. The illustration shows a diagram with the axis 27 for the wavelength and the axis 28 for the transmissivity of a glass. As it is known, glasses have a so-called >>UV edge<<, that is to say the wavelength range in which its transmittance declines abruptly towards zero when shifting to shorter wavelengths. In the illustration the curve 291 denotes the transmissivity of purest silica glass at a wavelength of 300 nm, the curve being marked by the dashed line 272 and the point 2911 on the curve 291, whereby the transmissivity remains high.

The curve 292 shows the course of the transmissivity of silica glass having impurities; at the same wavelength according to line 272 the transmissivity in this case has already declined to the point 2921. The curves 293 and 294 show sodium silicate glasses with increasing proportions of foreign oxides and the corresponding points 2931 and 2941 show the strong decrease in the transmissivity. This absorption of radiation in this area of the UV spectrum is predominantly triggered by stimulating the oxygen atoms in the silicate lattice to oscillate, whereas this stimulation is all the more shifted towards the range of lower wavelengths, the more the oxygen atoms are free to oscillate. It is known that alkaline oxides like e.g. sodium oxide are so-called lattice breakers, that is to say they break the three-dimensional lattice of the Si—O-bonds in places and thereby produce terminal oxygen ions.

At a wavelength of 400 nm, which corresponds to the dashed line 271 in the diagram of FIG. 10, all curves at the point 2942 are located in the high level of transmissivity. Thus, if the curve evaluation is conducted in an analogous manner to the method shown in FIG. 6 for both wavelengths, conclusions can be drawn from the ratio of the intensities on the degree of the decrease in transmissivity and thus on the chemical composition of a glass surface, since the transmissivity is an essential part of the emission behavior of a surface. As the lattice oscillations of silicate glasses also change as a function of their crystallinity degree, the displacement of the UV-pitch can also be used for measuring the crystallinity degree at a given composition, which is of importance with regard to e.g. firing processes of glasses with subsequent heat treatment, e.g. when being used in the dental area where glass ceramics with a specific crystallinity are used for producing aesthetically favorable effects (opalescence).

This method alternative, in which a measurement is effected simultaneously for more than two wavelength ranges or apart from the intensity value the color value of each pixel is determined as well, is of particular interest, since in some cases it allows separating the changes in the topography of the test specimen from changes in the material composition of the surface from each other using special evaluation algorithms. Changes in the topography have similar effects with all wavelengths of a pixel, that is to say in the absence of chemical changes, the intensity curves ascertained for different wavelengths show a similar profile; in contrast to this, the intensity ratio changes in the course of such a reaction and can, for instance, be illustrated by plotting the quotient of the intensity of two wavelengths as a curve against time.

The use of a collimator for concentrating the radiation of the two radiation sources 15' and 15" in FIG. 9 is important due to the fact that an exact ratio of the radiation intensity at two wavelengths irrespective of the local deviations of the topography can only be ascertained, if the irradiation of the two wavelengths takes place along the same optical axis.

Figure 11:
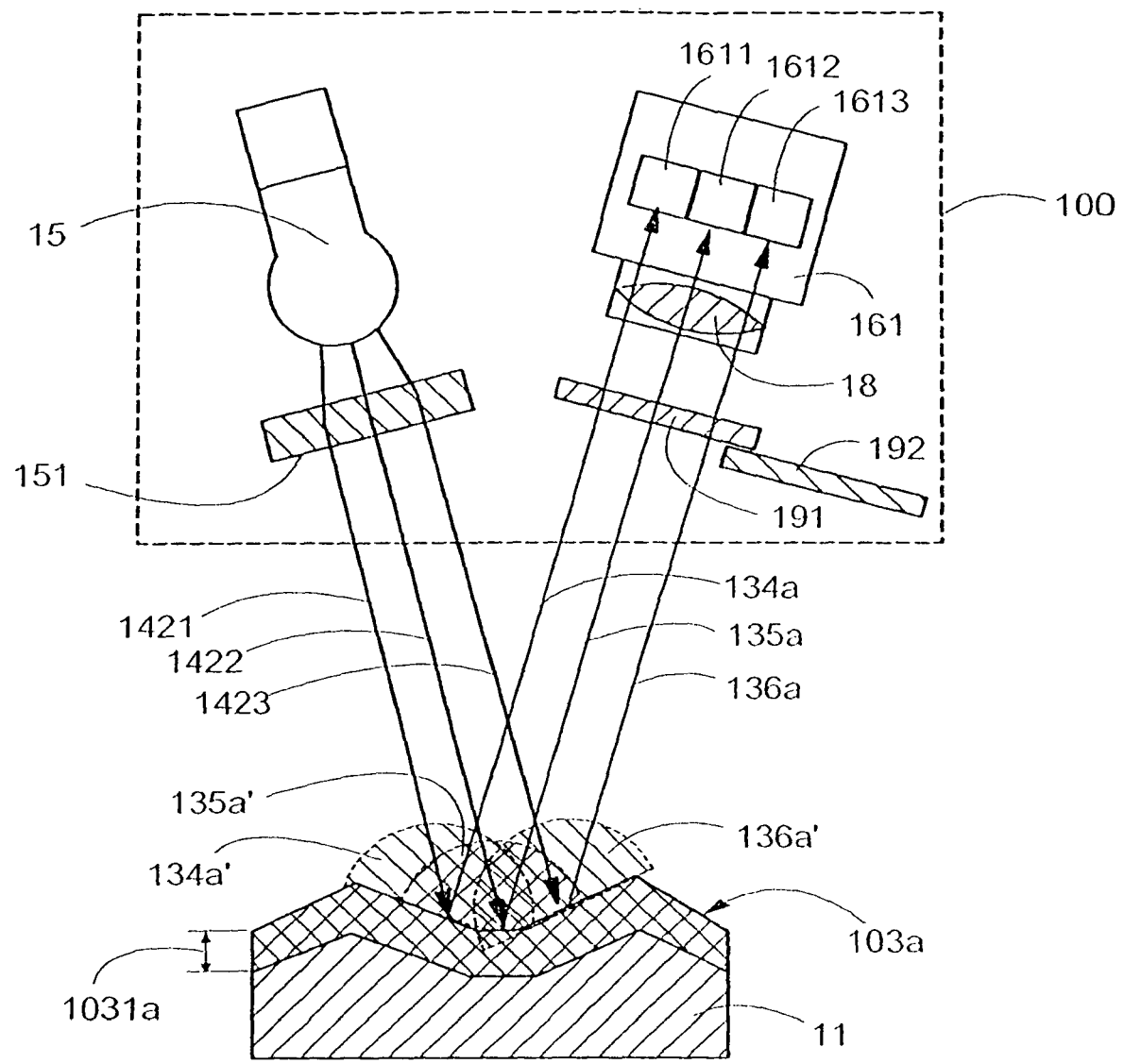
FIG. 11 shows a diagrammatic illustration of a modification of the second embodiment of the method of the invention that uses optical filters.

FIG. 11 shows an alternative of the method alternative shown in FIG. 9, which also operates on two wavelengths, in this case, however, a broadband UV lamp is used which comprises the wavelength range of at least one part of the UV edge. If a sensor matrix 161 is used that is a broadband sensor matrix as well, the determination of the intensity of the two wavelengths can be effected in such a manner that the optical filters 191 and 192 are periodically pushed into the optical or beam path which results in an respective absorption of a certain range of the UV radiation. As a matter of course, however, when using a broadband radiation source 15, it is also possible to do without the optical filters 191 and 192 and to use instead only the wavelength ranges of the video signal necessary for the identification in the evaluation process. As described before, however, apart from the intensity change (e.g. luminance), the deviation of the color value (e.g. chrominance) can also be used.

Figure 12:
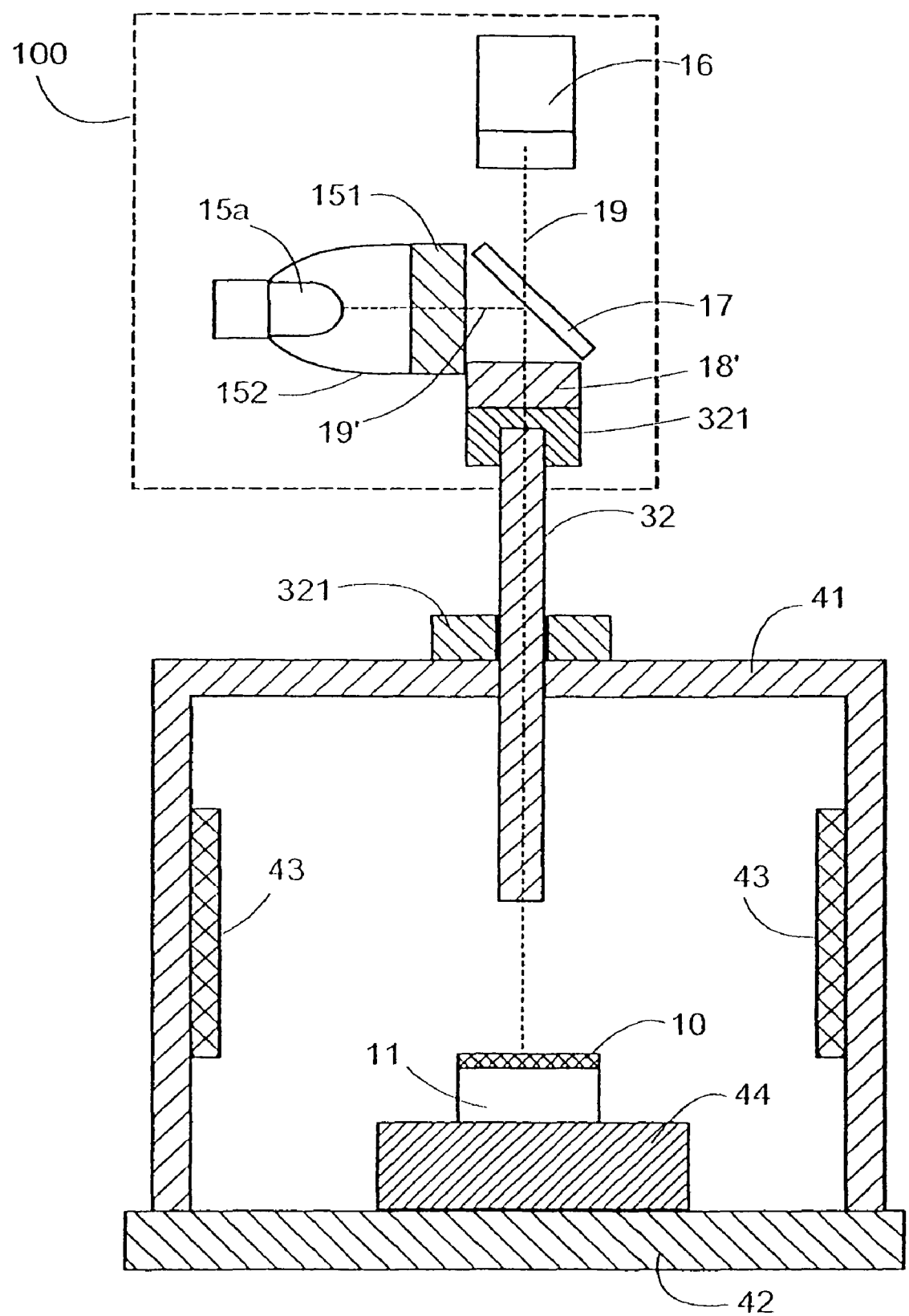
FIG. 12 shows a diagrammatic illustration of a modification of the second embodiment of the method according to the invention that uses one optical waveguide.

FIG. 12 shows another alternative of the second embodiment of the method according to the invention, which uses—analogously to device shown in FIG. 4*b*—a semipermeable mirror 17 for bringing the radiation of a radiation source 15*a*—in the present example a blue light LED having a reflector 152 and a collimator 151 connected ahead—on the same optical axis which is also used by the measurement device 16. Subsequent to the semipermeable mirror 17, the light is guided through a lens system 18' and a connecting part 321 into an optical wave guide 32 that consists of a quartz glass rod in the present example, which is vacuum-tightly guided into a furnace via a flange 322.

Of course, a conventionally used fiber bundle can also be used as optical wave guide. Since the present case is only about the possibility to guide or direct the radiation into the inner chamber of a furnace in a compact and temperature-resistant manner, or respectively to arrange the heat sensitive components of the system 100 that need much space, elegantly outside the furnace, the use of an inflexible or rigid optical waveguide in the form of a temperature-resistant quartz rod is particularly advantageous. The use of a flexible fiber bundle can also be imagined as being especially advantageous with a device built up analogously to FIG. 5, where the optical wave guide is mounted in the universal joint 32 instead of the measuring device, so that the remaining components of the optical system 100 can be fixedly mounted irrespective of the movement of the universal joint.

Figure 13:
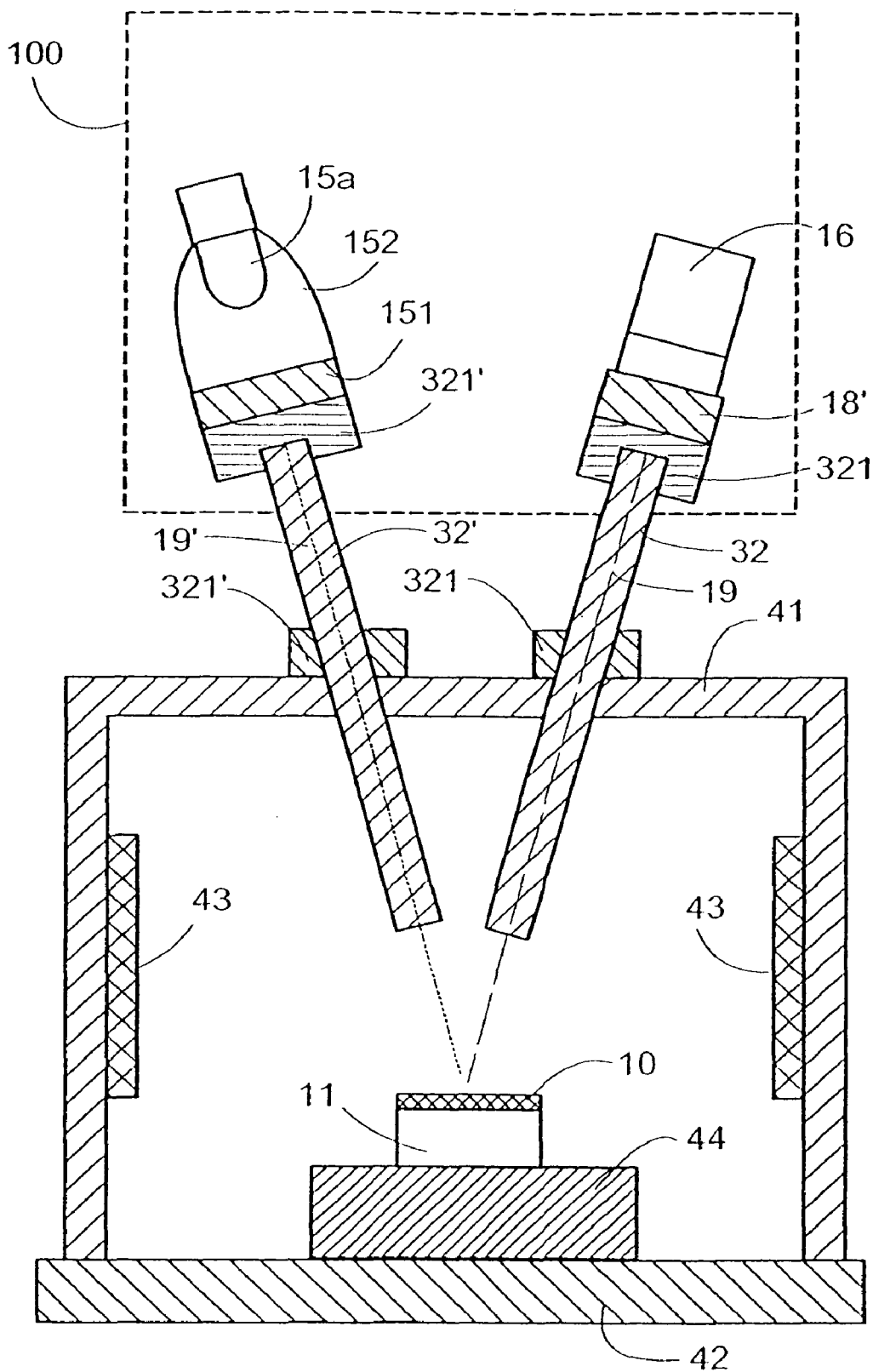
FIG. 13 shows a diagrammatic illustration of a modification of the second embodiment of the method according to the invention that uses two optical waveguides.

FIG. 13 shows another alternative of a device according to the invention, which, contrary to the device of FIG. 12, refrains from using a semipermeable mirror and guides instead the radiation supplied by the radiation source 15a as well as the radiation reflected from the surface 10 to the measuring device via optical wave guides 32 and 32', preferably in the form of quartz rods, whereas both optical wave guides are connected via coupling elements 321 and 321' with the remaining parts of the optical system. This device allows a larger radiation yield by doing without the semipermeable mirror, whereby the optical axes of the radiation source 15a and the measuring device 16, however, have to interface exactly on the surface 10 of the body 11.

The use of optical wave guides, of course, is not restricted to individual detectors, as shown in FIGS. 12 and 13, but instead of these individual detectors a sensor matrix, e.g. a video camera, can analogously also be provided.

The invention claimed is:

1. A method for optically monitoring the progression of a physical and/or chemical process taking place on a surface of a body, the process being a thermally activated process of firing a dental restoration part, in which a temporal profile of the intensity of a surface radiation, which emanates from part of the surface, is measured with the aid of a measuring device, wherein the measuring device is a sensor, wherein the change in the reflected portion of the radiation (14), which emanates from an extraneous source, is measured through the change in intensity of the surface radiation (13), and wherein the beginning of the process is ascertained by determining a discontinuity in the intensity curve of the surface radiation (13), said intensity curve running continuously before the start of the process, and wherein the end of the process is ascertained by determining a discontinuity of the intensity curve, said intensity curve of the surface radiation (13) running continuously after the end of the process, and wherein zero, maxima and minima of the first and/or second derivative of the intensity curve are used in order to determine the beginning and the end of the process and to characterize the profile of the curve.

2. The method as claimed in claim 1, wherein the extraneous source is one or more bodies of the natural surroundings of the surface (10), comprising a hotter furnace heating coil or colder furnace walls, which do not form a radiation equilibrium with the surface (10).

3. The method as claimed in claim 1, wherein the extraneous source is a radiation source (15) located outside the furnace (20), said radiation source having a spectrum differing from the natural spectrum of the radiation (13) of the surface (10).

4. The method as claimed in claim 1, wherein the intensity curve is plotted against time or the temperature, and said profile of the curve is used to control the process through at least one parameter influencing it.

5. The method of claim 4 wherein the parameter influencing the profile of the curve is the heating power of a furnace.

6. The method as claimed in claim 1, wherein the temporal profile of the intensity of the surface radiation is simultaneously determined for at least two wavelengths in a simultaneous manner and wherein changes in the ratios of these intensities or the change in the color value of the surface radiation (13) are used as an indication of the change in the structural architecture of the material structure and/or the chemical composition of the surface (10).

7. The method as claimed in claim 1, wherein the surface radiation (13) is measured with the aid of several sensors arranged in the form of a pixel matrix, the progression of the intensity and the progression of the color value being measured for each individual detector and being analyzed in the form of a curve, whereby the joint analysis of all curves as part of an image analysis provides additional information about the change in topography of the surface (10) during the course of the reaction.

8. The method as claimed in claim 1, wherein the physical and/or chemical process is a thermally activated process such as a phase transformation, a heat treatment, a thermochemical process, a sintering process of ceramic, vitreous, metallic, metal-ceramic or polymeric materials, a polymerization process taking place under the influence of temperature or radiation, or a combination of one or more of these processes.

9. A method as claimed in claim 8, wherein the sintering process is a firing process taking place in a dental firing furnace.

10. A method as claimed in claim 8, wherein the polymerization process is a reaction triggered by UV irradiation, the illumination necessary for the polymerization process being selected as radiation source (15) and a wavelength range that lies within the range of this radiation source (15) being selected for the detector.

11. A method as claimed in claim 1, wherein at the same time of determining the intensity of the surface radiation (13), also the temperature in the vicinity to or on a spot of the surface (10) is determined with the aid of a voltage-forming or current-forming method, with the aid of a thermocouple or a temperature-dependent resistance or with the aid of an optical measurement taking place in the infrared range.

12. A method as claimed in claim 11, wherein one of the channels of a quotient pyrometer is used to determine the intensity of the surface radiation (13), the combination of the measured values of both channels in a conventional manner being used to determine the temperature.

13. An apparatus for optically monitoring the progression of a physical and/or chemical process taking place on a surface (10) of a body (11), the process being a thermally activated process of firing a dental restoration part, in which a temporal profile of the intensity of a surface radiation, which emanates from part of the surface, is measured, said apparatus having a measuring device (16), wherein the measuring device comprises a sensor, which is at a distance from the surface (10), to measure the intensity and a color value of the surface radiation (13) coming from the surface (10), a processor configure to calculate the begging of the process by determining a discontinuity in the intensity curve of the surface radiation (13), said intensity curve running continuously before the start of the process, and wherein the end of the process is ascertained by determining a discontinuity of the intensity curve, said intensity curve of the surface radiation (13) running continuously after the end of the process, and wherein zero, maxima and minima of the first and/or second derivative of the intensity curve are used in order to determine the beginning and the end of the process and to characterize the profile of the curve.

14. The apparatus as claimed in claim 13 wherein in addition to the measuring device (16) a radiation source (15), which is at a distance from the surface (10), emits radiation (14) onto the surface (10).

15. The apparatus as claimed in claim 14, wherein the radiation (142) emitted by the radiation source (15) reaches the surface (10) in form of directional radiation (141) after having passed a collimator.

16. The apparatus as claimed in claim 15, wherein the radiation (141) from the light source (15) to the surface (10) and the radiation (13) from the surface (11) to the measuring device (16) is effected by means of optical waveguides.

17. The apparatus as claimed in claim 14, wherein the light source (15) is a lamp with a broad wavelength range, a LED, a halogen lamp or a laser.

18. The apparatus as claimed in claim 14, wherein the radiation source (15) and the measuring device (16) comprise optical axes that are angled relative to one another and that interface on the surface (10), as a result of which a reproducible portion of the radiation emitted by the light source (15) can be detected with the aid of the measuring device (16).

19. The apparatus as claimed in claim 14, wherein the optical axes of the radiation source (15) and the measuring device (16) interface in a semipermeable mirror (17) and have the same optical axis from the mirror to the surface (10).

20. The apparatus as claimed in claim 19, wherein the radiation source (15) and the measuring device (16) are mounted on the outside of a furnace and wherein the optical axes thereof are guided to the surface (10) via one or two openings that are sealed off to the outside by means of vacuum-tight windows.

21. The apparatus as claimed in claim 20, wherein the radiation source (15) and the measuring device (16) are arranged on a common holder, said holder and thus the optical axes (19) and (19') being able to be rotated in at least one direction with the aid of at least one hinge apparatus.

22. The apparatus as claimed in claim 13, wherein the measuring device (16) comprises focusing optics.

23. The apparatus as claimed in claim 13, wherein the measuring device (16) is an electronic image detecting unit having a light-sensitive chip, a camera or video camera.

* * * * *